United States Patent
Nguyen

(10) Patent No.: US 9,695,189 B2
(45) Date of Patent: *Jul. 4, 2017

(54) CHEMICAL CROSSLINKERS AND COMPOSITIONS THEREOF

(71) Applicant: Mark Quang Nguyen, San Jose, CA (US)

(72) Inventor: Mark Quang Nguyen, San Jose, CA (US)

(73) Assignee: Mark Quang Nguyen, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/782,584

(22) Filed: Mar. 1, 2013

(65) Prior Publication Data

US 2014/0249319 A1     Sep. 4, 2014

(51) Int. Cl.
| | | |
|---|---|---|
| *C07D 495/04* | (2006.01) | |
| *C07C 329/06* | (2006.01) | |
| *C07D 207/452* | (2006.01) | |
| *C07D 207/46* | (2006.01) | |
| *C07D 403/12* | (2006.01) | |
| *C07D 405/12* | (2006.01) | |
| *C07D 493/04* | (2006.01) | |
| *C07D 233/32* | (2006.01) | |

(52) U.S. Cl.
CPC .......... *C07D 495/04* (2013.01); *C07C 329/06* (2013.01); *C07D 207/452* (2013.01); *C07D 207/46* (2013.01); *C07D 233/32* (2013.01); *C07D 403/12* (2013.01); *C07D 405/12* (2013.01); *C07D 493/04* (2013.01); *C07C 2601/14* (2017.05)

(58) Field of Classification Search
CPC .. C07D 207/46; C07D 413/12; C07D 495/04; C07D 405/12
USPC .......................... 548/303.7, 314.7, 520, 542
See application file for complete search history.

(56) References Cited

PUBLICATIONS

Arukwe et al. Acta Chemica Scandinavica 1999, 53, 594-601.*
CAS Registry Entry for Registry No. 133217-82-0, which entered STN on Apr. 12, 1991.*
CAS Registry Entry for Registry No. 1162207-28-4, which entered STN on Jul. 13, 2009.*
CAS Registry Entry for Registry No. 1085654-64-3, which entered STN on Dec. 17, 2008.*
CAS Registry Entry for Registry No. 1085648-42-5, which entered STN on Dec. 17, 2008.*
Mollica et al. Protein & Peptide Letters 2012, 19, 1245-1249.*
CAS Registry Entry for Registry No. 151228-84-1, which entered STN on Nov. 16, 1993.*
CAS Registry Entry for Registry No. 208246-33-7, which entered STN on Jul. 9, 1998.*
CAS Registry Entry for Registry No. 1085806-86-5, which entered STN on Dec. 17, 2008.*

* cited by examiner

*Primary Examiner* — Matthew Coughlin

(57) ABSTRACT

Cleavable crosslinkers of Formula (I) useful reagents in biochemical drug research and development such as antibody drug conjugates are disclosed.

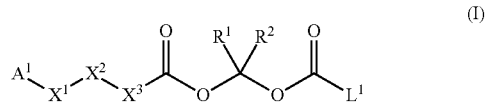

9 Claims, No Drawings

CHEMICAL CROSSLINKERS AND COMPOSITIONS THEREOF

This nonprovisional utility patent application claims the benefit of a prior provisional patent application No. 61/622,639 filed on Apr. 11, 2012.

FIELD

The disclosure relates to multi-functional chemical crosslinkers having a functional group that can form a cleavable bond with amine-containing molecules upon exposure to esterases and/or under basic conditions.

BACKGROUND

Chemical crosslinkers are useful reagents in biochemical research and development. They are use to study protein-protein interaction, to attach small molecule (e.g., a drug) to a larger molecule (e.g., an antibody) as in antibody-drug conjugate, and to immobilize molecule (e.g., a drug, a peptide, an oligonucleotide, and a protein) to a substrate (e.g., a glass surface, a gold nanoparticle, and a polystyrene bead) in biochemical kits and assays.

Most chemical crosslinkers form non-cleavable bonds through amide and/or thioether functional groups. Only a few crosslinkers are capable of forming cleavable functional group. However, most of these cleavable crosslinkers require harsh conditions. Bis(2-[succinimidooxycarbonyloxyl]ethyl)-sulfone (BSOCOES) requires strong basic condition (pH 11.6 for 2 hours at 37° C.) to cleave the carbamate groups, disuccinimidyl tartarate (DST) requires periodate oxidation, and dithiobis-maleimidoethane (DTME) requires mecaptoethanol or dithiothreitol.

SUMMARY

Thus, there is a need for new crosslinkers having a functional group that can form a cleavable bond with amine-containing molecules upon exposure to esterases and/or under basic conditions.

Crosslinkers, intermediates of crosslinkers, and methods of synthesizing the crosslinkers and intermediates are disclosed.

In a first aspect compounds of Formula (I) are disclosed:

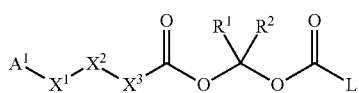

(I)

or a salt thereof, wherein:

$A^1$ is selected from a thiol-reactive group, an amine-reactive group, an avidin-binding group, a photoreactive group, an alkyne-reactive group, and an azide-reactive group;

$X^1$ and $X^3$ are independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —$(CH_2)_{n1}$—$(CH_2$—$CH_2$—$O)_{n2}$—$(CH_2)_{n3}$—, wherein:

each n1 and n3 is independently an integer selected from 0 to 5; and each n2 is independently an integer selected from 1 to 25;

$X^2$ is selected from a covalent bond, —O—, —S—, —N—, —N=, —N=N—, —N=C—, —SO—, —SO$_2$—, —SO$_2$N—, —SS—, —C(O)—, —C(O)O—, —C(O)N—, —C(O)S—, —C(O)N—N=, —OP(O)(OH)O—, —OC(O)O—, —OC(O)N—, —NC(O)N—, and —NC(S)N;

$R^1$ and $R^2$ are independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl; and $L^1$ is selected from halogen, N-hydroxysuccinimidyl, substituted N-hydroxysuccinimidyl, phenol-yl, substituted phenol-yl, hydroxybenzotriazolyl, substituted hydroxybenzotriazolyl, imidazolyl, and substituted imidazolyl.

In a second aspect, methods of synthesizing compounds of Formula (I), or a salt thereof are disclosed.

DETAILED DESCRIPTION

Definitions

A dash ("-") that is not between two letters or symbols is used to indicate a point of attachment for a substituent. For example, —$CONH_2$ is attached through the carbon atom.

Compounds provided by the present disclosure are encompassed by structural formulae disclosed herein and include any specific compounds within these formulae. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to one skilled in the art. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. Accordingly, compounds may be hydrated, solvated, or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

The term "acyl" means an H—C(O)—, alkyl-C(O)—, or cycloalkyl-C(O)— group wherein alkyl and cycloalkyl are as defined herein. In certain embodiments, an acyl group is $C_{1-8}$ acyl, $C_{1-6}$ acyl, $C_{1-4}$ acyl, and in certain embodiments, $C_{1-3}$ acyl.

The term "alkanearene" refers to a hydrocarbon group in which an alkyl group is bonded to an aromatic group, wherein alkyl and aromatic group are as defined herein. In certain embodiments, an alkanearene group is $C_{7-20}$ alkanearene, $C_{7-12}$ alkanearene, and in certain embodiments $C_{7-10}$ alkanearenediyl.

The term "alkanearenediyl" refers to a diradical hydrocarbon group derived by the removal of two hydrogen atoms from a single carbon atom or by the removal of a single hydrogen atom from two carbon atoms from a parent alkanearene group. In certain embodiments, an alkanearenediyl group is $C_{7-20}$ alkanearenediyl, $C_{7-12}$ alkanearenediyl, and in certain embodiments $C_{7-10}$ alkanearenediyl.

The term "alkanediyl" refers to a diradical of a saturated or unsaturated, branched, or straight-chain acyclic hydrocarbon group, having, for example, from 1 to 20 carbon atoms, from 1-10 carbon atoms, from 1-6 carbon atoms, from 1 to 4 carbon atoms, or from 1 to 3 hydrocarbon atoms. Examples of alkanediyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, decane-1,10-diyl, dodecane-1,12-diyl, and the like.

The term "alkanecycloalkane" refers to a hydrocarbon group in which an alkyl group is bonded to a cycloalkane group, wherein alkyl and cycloalkane are as defined herein. In certain embodiments, an alkanecycloalkane group is $C_{7-20}$ alkanecycloalkane, $C_{7-12}$ alkanecycloalkane, and in certain embodiments $C_{7-10}$ alkanecycloalkane. In certain embodiments an alkanecycloalkane is selected from methylcyclohexane:

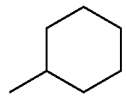

The term "alkanecycloalkanediyl" refers to a diradical hydrocarbon group derived by the removal of two hydrogen atoms from a single carbon atom or by the removal of a single hydrogen atom from two carbon atoms from a parent alkanecycloalkane group. In certain embodiments an alkanecycloalkanediyl is selected from 4-methylcyclohexanediyl:

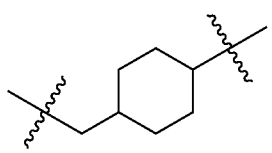 [SMILES: *CC1CCC(*)CC1]

The term "alkoxy" refers to an alkyl-O— group where alkyl is as defined herein. Examples of alkoxy groups include methoxy, ethoxy, n-propoxy, isopropoxy, and n-butoxy. In certain embodiments, an alkoxy group is $C_{1-8}$ alkoxy, $C_{1-6}$ alkoxy, $C_{1-4}$ alkoxy, and in certain embodiments $C_{1-3}$ alkoxy.

The term "alkyl" refers to a monoradical of a saturated or unsaturated, branched, or straight-chain acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. Examples of alkyl groups include methyl, ethyl, n-propyl, iso-propyl, n-butyl, iso-butyl, n-hexyl, n-decyl, tetradecyl, and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds.

The term "alkyne-reactive group" as used herein refers to a functional group capable of reacting with an alkyne in the presence or absence of a catalyst to form a triazole. Example of a catalyst includes Copper(I). Examples of alkyne-reactive groups include an azide group. In certain embodiments, an alkyne-reactive group is selected from Formula (A$^1$e1), Formula (A$^1$e2), and Formula (A$^1$d3):

(A$^1$e1)

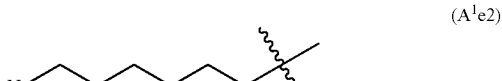

(A$^1$e2)

and

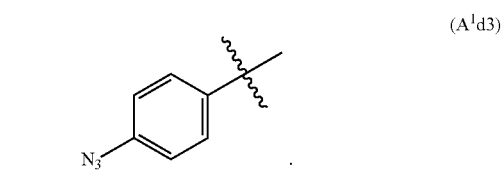

(A$^1$d3)

The term "amine-reactive group" as used herein refers to a functional group capable of reacting with a primary amine group, a secondary amine group, a hydrazine group, or a substituted hydrazine group to form an amide bond, a urea bond, a thiourea bond, a sulfonamide bond, a carbamate bond, an imine, or a hydrazone. Examples of an amine-reactive group include an aldehyde group, a ketone group, an NHS-ester group, a substituted phenylester group, an isocyanate group, an isothiocyanate group, and an alkyl imidate group. In certain embodiments, an amine-reactive group is selected from Formula (A$^1$b1), Formula (A$^1$b2), Formula (A$^1$b3), and Formula (A$^1$b4):

(A$^1$b1)

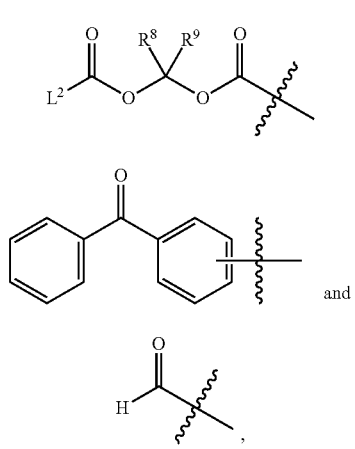

wherein each $R^8$ and $R^9$ is independently selected from hydrogen, $C_{1-4}$ alkyl, substituted $C_{1-4}$ alkyl, $C_{1-4}$ heteroalkyl, substituted $C_{1-4}$ heteroalkyl, $C_{6-10}$ aryl, substituted $C_{6-10}$ aryl, $C_{6-10}$ heteroaryl, and substituted $C_{6-10}$ heteroaryl; and $L^2$ is a leaving group such as a halogen, an N-hydroxysuccinimidyl, a substituted N-hydroxysuccinimidyl, a phenol-yl, a substituted phenol-yl, a hydroxybenzotriazolyl, a substituted hydroxybenzotriazolyl, an imidazolyl, and a substituted imidazolyl.

The term "amino acid side chain" includes the side chains of naturally occurring standard amino acids, side chains of naturally occurring non-standard amino acids, and side chains of non-naturally occurring amino acid derivatives. In certain embodiments, amino acid side chain includes naturally occurring standard amino acid side chains.

The term "arenediyl" refers to an aromatic hydrocarbon diradical derived by the removal of two hydrogen atoms from a single carbon atom or by the removal of a single hydrogen atom from two carbon atoms of a parent aromatic ring system. In certain embodiments, an arenediyl group is $C_{6-20}$ arenediyl, $C_{6-12}$ arenediyl, $C_{6-10}$ arenediyl, and in certain embodiments, $C_{6-8}$ arenediyl. Examples of arenediyl groups include benzene-1,2-diyl, benzene-1,3-diyl, benzene-1,4-diyl, naphthalene-1,6-diyl, and the like.

The term "aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

The term "avidin-binding group" as used herein refers to a biotin, a biotin derivative such as desthiobiotin, iminobiotin, bisnorbiotin, tetranorbiotin, biotin sulfoxide, biotin sulfone, and iminobiotin trifluoroacetamide, or a Strep-tag (a synthetic peptide consisting of an N-terminal or C-terminal eight amino acid sequence: Trp-Ser-His-Pro-Gln-Phe-Glu-Lys) capable of binding to avidin, deglycosylated avidin, streptavidin, Strep-Tactin or related proteins. In certain embodiments, an avidin-binding group is selected from Formula ($A^1c1$), Formula ($A^1c2$), and Formula ($A^1c3$):

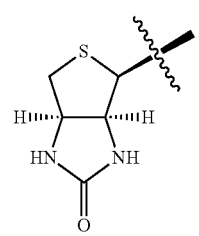

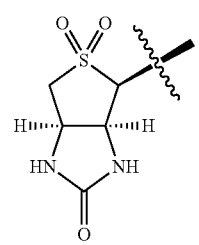

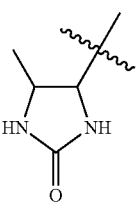

The term "azide-reactive group" as used herein refers to a functional group capable of reacting with an azide in the presence or absence of a catalyst to form a triazole. Example of a catalyst includes Copper(I). Examples of azide-reactive groups include a terminal alkyne group and an internal alkyne group. In certain embodiments, an azide-reactive group is selected from Formula ($A^1f1$), Formula ($A^1f2$), Formula ($A^1f3$), Formula ($A^1f4$), and Formula ($A^1f5$):

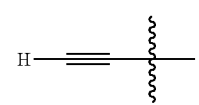

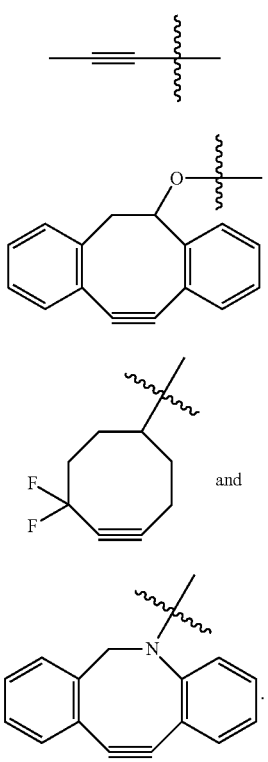

The term "crosslinker" as used herein refers to any chemical agent that joins two or more molecules through covalent bond(s) or through strong hydrogen-bonding(s).

The term "cycloalkane" refers to a saturated or partially saturated cyclic or polycyclic hydrocarbon group. In certain embodiments, a cycloalkane group is $C_{3-12}$ cycloalkane, $C_{3-8}$ cycloalkane, $C_{3-6}$ cycloalkane, and in certain embodiments, $C_{5-6}$ cycloalkane.

The term "cycloalkanediyl" refers to a diradical cyclic or polycyclic hydrocarbon group. In certain embodiments, a cycloalkane-diyl group is $C_{3-12}$ cycloalkane-diyl, $C_{3-8}$ cycloalkane-diyl, $C_{3-6}$ cycloalkanediyl, and in certain embodiments, $C_{5-6}$ cycloalkanediyl. Examples of cycloalkanediyl groups include cyclohexane-1,4-diyl, cyclohexane-1,3-diyl, and cyclohexane-1,2-diyl.

The term "cycloalkyl" refers to a saturated or unsaturated cyclic or polycyclic hydrocarbon monoradical group. In certain embodiments, a cycloalkyl group is $C_{3-12}$ cycloalkyl, $C_{3-8}$ cycloalkyl, $C_{3-6}$ cycloalkyl, and in certain embodiments, $C_{5-6}$ cycloalkyl.

The term "heteroalkanearenediyl" refers to an alkanearenediyl group in which one or more of the carbon atoms are replaced with a heteroatom (e.g., N, O, S, P, or Si).

The term "heteroalkanecycloalkanediyl" refers to an alkanecycloalkanediyl group in which one or more of the carbon atoms are replaced with a heteroatom (e.g., N, O, S, P, or Si).

The term "heteroalkanediyl" refers to an alkanediyl group in which one or more of the carbon atoms is replaced with a heteroatom (e.g., N, O, S, P, or Si).

The term "heteroalkyl" refers to an alkyl group in which one or more of the carbon atoms are replaced with a heteroatom (e.g., N, O, S, P, or Si).

The term "heteroarenediyl" refers to an arenediyl group wherein one or more of the carbon atoms are replaced with a heteroatom (e.g., N, O, S, P, or Si). Examples of heteroarenediyl groups include furane-diyl and pyridine-diyl.

The term "heteroaryl" refers to an aryl group wherein one or more of the ring carbon atoms are replaced with a heteroatom (e.g., N, O, S, P, or Si). Examples of heteroaryl groups include, but are not limited to, monoradicals of acridine, arsindole, carbazole, f3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is $C_{5-20}$ heteroaryl, $C_{5-12}$ heteroaryl, $C_{5-8}$ heteroaryl, and in certain embodiments, $C_{5-6}$ heteroaryl. In certain embodiments heteroaryl groups are those derived from thiophene, pyrrole, benzothiophene, benzofuran, indole, pyridine, quinoline, imidazole, oxazole, and pyrazine.

The term "heterocycloalkanediyl" refers to a cycloalkanediyl group in which one or more of the carbon atoms are replaced with a heteroatom (e.g., N, O, S, P, or Si).

The term "heterocycloalkyl" refers to a cycloalkyl group in which one or more of the carbon atoms are replaced with a heteroatom (e.g., N, O, S, P, or Si).

The term "ligand" as used herein refers to an organic compound or inorganic substrate that contains or is functionalized to contain at least one thiol group, at least one primary amine group, at least one secondary amine group, at least one biotin-binding group, at least one photoreactive group, at least one alkyne group, at least one azide group, or a combination of any of the foregoing. The function of the ligand, for example, is to prolong the in-vivo half-life of the drug, reduce dosing frequency, lower toxicity, enhance the targeted delivery of the drug, and/or enable parallel in-vitro analysis. The inorganic substrate may be, for example, a glass bead or surface and a gold bead or surface, The organic compound may be, for example, a $C_{6-20}$ hydrocarbon, a natural or modified peptide, a natural or modified protein, a natural or modified antibody, a natural or modified nucleoside, a natural or modified nucleotide, a natural or modified oligonucleotide, a sugar, a natural or modified oligosaccharide, an aminoglycoside (antibiotic), or a natural or modified polymer or copolymer such as a polylactide, a polystyrene surface, a polystyrene bead, a dendrimer, a polyalkylene oxide, or a polyethylene oxide. A ligand can contain a thiol group, an amine group, a biotin-binding group, an alkyne group, an azide group, and/or a photoreactive group, or may be functionalized to contain thiol group, an amine group, a biotin-binding group, an alkyne group, an azide group, and/or a photoreactive group.

Examples of peptides include glutathione, carnosine, and pantethine.

Examples of proteins include bovine serum albumin, human serum albumin, avidin, and strepavidin.

Examples of antibodies include polyclonal antibodies, monoclonal antibodies, murine monoclonal antibodies, chimeric monoclonal antibodies, fusion proteins, humanized monoclonal antibodies, and human monoclonal antibodies. In certain embodiments, an antibody is a humanized monoclonal antibody and is selected from Afutuzumab, Alemtuzumab, Bevacizumab, Bivatuzumab, Cantuzumab, Citatuzumab, Dacetuzumab, Elotuzumab, Etaracizumab, Farletuzumab, Gemtuzumab ozogamicin, Inotuzumab ozogamicin, Labetuzumab, Lintuzumab, Matuzumab§, Milatuzumab, Nimotuzumab, Oportuzumab monatox, Pertuzumab, Sibrotuzumab, Tacatuzumab tetraxetan, Tigatuzumab, Trastuzumab, Tucotuzumab celmoleukin, Veltuzumab, Aselizumab, Apolizumab, Benralizumab, Cedelizumab, Certolizumab, Daclizumab, Eculizumab, Efalizumab, Epratuzumab, Erlizumab, Fontolizumab, Mepolizumab, Natalizumab, Ocrelizumab, Omalizumab, Pascolizumab, Pexelizumab, PRO 140, Reslizumab, Rontalizumab, Rovelizumab, Ruplizumab, Siplizumab, Talizumab, Teplizumab, Tocilizumab, Toralizumab, Vedolizumab, Visilizumab, TGN1412, Ibalizumab, Tefibazumab, Alacizumab pegol, Bevacizumab/Ranibizumab, Etaracizumab, Tadocizumab, Bapineuzumab, Solanezumab, Tanezumab, Urtoxazumab, Felvizumab, Motavizumab, Palivizumab, Lebrikizumab, and Ranibizumab. In certain embodiments, an antibody is a murine monoclonal antibody and is selected from Abagovomab, Igovomab, Oregovomab, Afelimomab, Elsilimomab, Faralimomab, Gavilimomab, Inolimomab, Maslimomab, Nerelimomab, Odulimomab, Telimomab aritox, Vepalimomab, Zolimomab aritox, Altumomab pentetate, Anatumomab mafenatox, Arcitumomab, Bectumomab, Blinatumomab, CC49, Detumomab, Ibritumomab tiuxetan, Minretumomab, Mitumomab, Naptumomab estafenatox, Nofetumomab merpentan, Pemtumomab, Pintumomab, Satumomab pendetide, Taplitumomab paptox, Tenatumomab, Tositumomab, 3F8, Besilesomab, Fanolesomab, Lemalesomab, Sulesomab, Biciromab, Imciromab, Capromab pendetide, Edobacomab, Edrecolomab, and Nacolomab tafenatox. In certain embodiments, an antibody is a chimeric monoclonal antibody and is selected from Bavituximab, Brentuximab vedotin, Cetuximab, Siltuximab, Rituximab, Abciximab, Volociximab, Basiliximab, Clenoliximab, Galiximab, Gomiliximab, Infliximab, Keliximab, Lumiliximab, Priliximab, Teneliximab, Vapaliximab, Ecromeximab, and Pagibaximab. In certain embodiments, an antibody is a human monoclonal antibody and is selected from Adalimumab, Atorolimumab, Fresolimumab, Golimumab, Lerdelimumab, Metelimumab, Morolimumab, Ipilimumab, Tremelimumab, Bertilimumab, Zanolimumab, Briakinumab, Canakinumab, Ustekinumab, Adecatumumab, Belimumab, Cixutumumab, Conatumumab, Figitumumab, Iratumumab, Lexatumumab, Lucatumumab, Mapatumumab, Necitumumab, Ofatumumab, Olaratumab, Panitumumab, Pritumumab, Robatumumab, Votumumab, Zalutumumab, Denosumab, Stamulumab, Efungumab, Exbivirumab, Foravirumab, Libivirumab, Rafivirumab, Regavirumab, Sevirumab, Tuvirumab, Nebacumab, Panobacumab, Raxibacumab, Ramucirumab, Gantenerumab, and Glembatumumab.

Examples of nucleosides include thymidine, cytidine, uridine, adenosine, and guanosine.

Examples of oligonucleotides include single-stranded and double-stranded oligoribonucleotides, oligoribonucleotide derivatives, oligodeoxyribonucleotides, and oligodeoxyribonucleotide derivatives such as phosphorothioates, phosphoramidates, and phosphorothioamidates.

Examples of oligonucleotides also include oblimersen and imetelstat.

Examples of sugars include glucosamine.

Examples of aminoglycosides include streptomycin, neomycin, framycetin, paromomycin, ribostamycin, kanamycin, amikacin, arbekacin, bekanamycin, dibekacin, tobramycin, spectinomycin, hygromycin B, paromomycin sulfate, gentamicin, netilmicin, sisomicin, isepamicin, verdamicin, and astromicin.

Examples of oligosaccharides include polyglucosamine (chitosan).

Examples of polymers include polyethylene glycol (PEG), monomethyl polyethylene glycol (MPEG), polypropylene glycol (PPG), polylactide, N-(2-hydroxypropyl) methacrylamide (HPMA) copolymer, and poly(styrene-co-maleic acid). In certain embodiments, the polymer is MPEG having a number average molecular weight from about 200 to about 60,000 Daltons, from about 1,000 to about 40,000 Daltons, and in certain embodiments, from about 2,000 to about 12,500 Daltons.

Examples of dendrimers include poly(amidoamine) dentrimers (PAMAM) and poly(propylenimine) dentrimers (PPI).

The term "parent aromatic ring system" refers to an unsaturated cyclic or polycyclic ring system having a conjugated π electron system. Included within the definition of "parent aromatic ring system" are fused ring systems in which one or more of the rings are aromatic and one or more of the rings are saturated or unsaturated, such as, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

The term "parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and xanthene.

The term "photoreactive group" as used herein refers to a functional group capable of reacting with a primary, secondary or tertiary amine upon exposure to actinic radiation, such as ultraviolet light, to form at least one covalent bond. Examples of photoreactive groups include an azide group, a diaziridine group, a coumarin group, and a psoralen group. In certain embodiments, a photoreactive group is selected from Formula ($A^1d1$), Formula ($A^1d2$), Formula ($A^1d3$), Formula ($A^1d4$), Formula ($A^1d5$), Formula ($A^1d6$), Formula ($A^1d7$), and Formula ($A^1d8$):

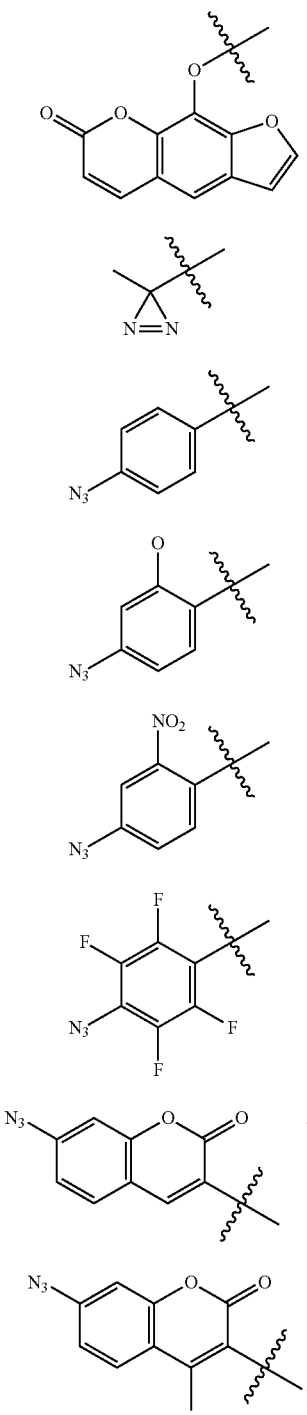

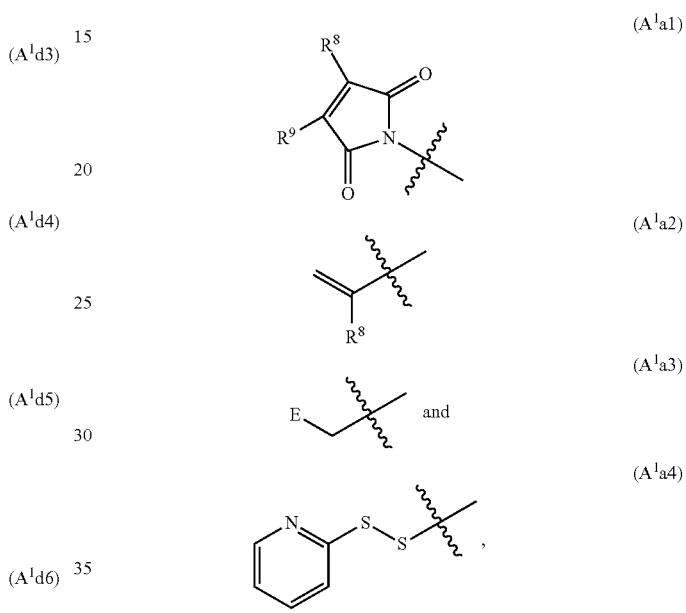

Examples of photoreactive groups are also disclosed in U.S. Publication No. 2001/00022761.

The term "substituted" refers to a group in which one or more hydrogen atoms are each independently replaced with the same or different substituent(s). In certain embodiments, a substituent is selected from halogen, —S(O)$_2$OH, —S(O)$_2$—C$_{1-6}$ alkyl, —SH, —S—C$_{1-6}$ alkyl, —COOH, —CONH$_2$, —N$_3$, —NO$_2$, —NH$_2$, —NH(C$_{1-6}$ alkyl), —N(C$_{1-6}$ alkyl)$_2$, —CN, =O, C$_{1-6}$ alkyl, —CF$_3$, —OH, C$_{6-8}$aryl, C$_{1-6}$ heteroalkyl, C$_{5-8}$heteroaryl, C$_{1-6}$ alkoxy, C$_{1-6}$ acyl, and —COR where R is C$_{1-6}$ alkyl. In certain embodiments, a substituent is chosen from —OH, —NH$_2$, and C$_{1-6}$ alkyl.

The term "thiol-reactive group" as used herein refers to a functional group capable of reacting with a thiol group to form a thiol ether bond, a disulfide bond, or a thiourea bond. Examples of a thiol-reactive group include a vinyl group (—CH=CH$_2$), a haloalkyl group, a haloacetyl group, and an isocyanate group (—NCO). In certain embodiments a thiol-reactive group is selected from Formula (A$^1$a1), Formula (A$^1$a2), Formula (A$^1$a3), and Formula (A$^1$a4):

wherein each R$^8$ and R$^9$ is independently selected from hydrogen, C$_{1-4}$ alkyl, substituted C$_{1-4}$ alkyl, C$_{1-4}$ heteroalkyl, substituted C$_{1-4}$ heteroalkyl, C$_{6-10}$ aryl, substituted C$_{6-10}$ aryl, C$_{6-10}$ heteroaryl, and substituted C$_{6-10}$ heteroaryl; and each E is selected from F, Cl, Br, and I.

Compounds are named using Symyx Draw 3.3, Symyx Solutions Inc., 2010.

Reference is now made in detail to certain embodiments of compounds, compositions, and methods. The disclosed embodiments are not intended to be limiting of the claims. To the contrary, the claims are intended to cover all alternatives, modifications, and equivalents.

Crosslinkers

In certain embodiments, a crosslinker has the structure of Formula (I):

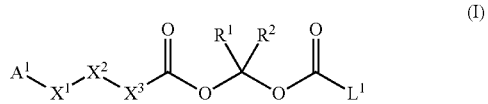

or a salt thereof, wherein:

A$^1$ is selected from a thiol-reactive group, an amine-reactive group, an avidin-binding group, a photoreactive group, an alkyne-reactive group, and an azide-reactive group;

$X^1$ and $X^3$ are independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and —(CH$_2$)$_{n1}$—(CH$_2$—CH$_2$—O)$_{n2}$—(CH$_2$)$_{n3}$—, wherein:

each n1 and n3 is independently an integer selected from 0 to 5; and each n2 is independently an integer selected from 1 to 25;

$X^2$ is selected from a covalent bond, —O—, —S—, —N—, —N=, —N=N—, —N=C—, —SO—, —SO$_2$—SO$_2$N—, —SS—, —C(O)—, —C(O)O—, —C(O)N—, —C(O)S—, —C(O)N—N=, —OP(O)(OH)O—, —OC(O)O—, —OC(O)N—, —NC(O)N—, and —NC(S)N;

$R^1$ and $R^2$ are independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl; and $L^1$ is selected from halogen, N-hydroxysuccinimidyl, substituted N-hydroxysuccinimidyl, phenol-yl, substituted phenol-yl, hydroxybenzotriazolyl, substituted hydroxybenzotriazolyl, imidazolyl, and substituted imidazolyl.

In certain embodiments of a compound of Formula (I), $A^1$ is a moiety selected from Formula ($A^1$a1), Formula ($A^1$a2), Formula ($A^1$a3), Formula ($A^1$b1), Formula ($A^1$b2), Formula ($A^1$c1), Formula ($A^1$c2), Formula ($A^1$c3), Formula ($A^1$d1), Formula ($A^1$d2), Formula ($A^1$d3), Formula ($A^1$e1), Formula ($A^1$f1), and Formula ($A^1$f2):

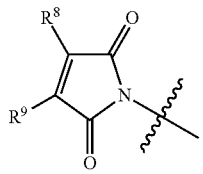
($A^1$a1)

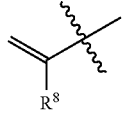
($A^1$a2)

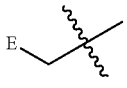
($A^1$a3)

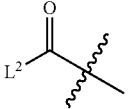
($A^1$b1)

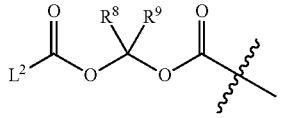
($A^1$b2)

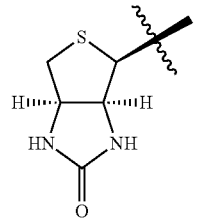
($A^1$c1)

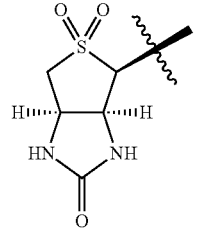
($A^1$c2)

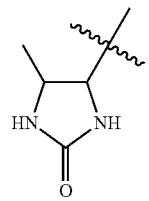
($A^1$c3)

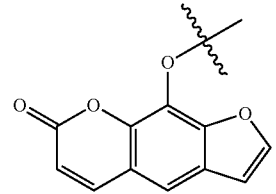
($A^1$d1)

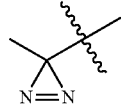
($A^1$d2)

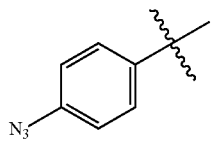
($A^1$d3)

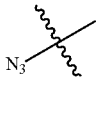
($A^1$e1)

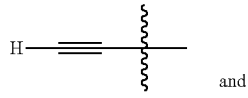
($A^1$f1)

and

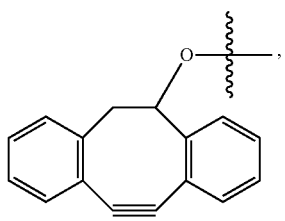
(A¹f2)

wherein:

each $R^8$ and $R^9$ is independently selected from hydrogen, $C_{1-4}$ alkyl, substituted $C_{1-4}$ alkyl, $C_{1-4}$ heteroalkyl, substituted $C_{1-4}$ heteroalkyl, $C_{6-10}$ aryl, substituted $C_{6-10}$ aryl, $C_{6-10}$ heteroaryl, and substituted $C_{6-10}$ heteroaryl;

E is selected from F, Cl, Br, and I; and $L^2$ is selected from halogen, N-hydroxysuccinimidyl, substituted N-hydroxysuccinimidyl, phenol-yl, substituted phenol-yl, hydroxybenzotriazolyl, substituted hydroxybenzotriazolyl, imidazolyl, and substituted imidazolyl.

In certain embodiments of Formula (I), $A^1$ is a thiol-reactive group, $A^1$ is an amine-reactive group, $A^1$ is an avidin-binding group, and in certain embodiments, $A^1$ is a photoreactive group, $A^1$ is an alkyne-reactive group, and $A^1$ is an azide-reactive group.

In certain embodiments of Formula (I), $A^1$ is a thiol-reactive group selected from Formula (A¹a1), Formula (A¹a2), and Formula (A¹a3). In certain embodiments of Formula (I), $A^1$ is an amine-reactive group selected from Formula (A¹b1) and Formula (A¹b2). In certain embodiments of Formula (I), $A^1$ is an avidin-binding group selected from Formula (A¹c1), Formula (A¹c2), and Formula (A¹c3). In certain embodiments of Formula (I), $A^1$ is a photoreactive group selected from Formula (A¹d1), Formula (A¹d2), and Formula (A¹d3). In certain embodiments of Formula (I), $A^1$ is an alkyne-reactive group selected from Formula (A¹e1). In certain embodiments of Formula (I), $A^1$ is an azide-reactive group selected from Formula (A¹f1) and Formula (A¹f2).

In certain embodiments of a compound of Formula (I), $A^1$ is Formula (A¹a1). In certain embodiments of a compound of Formula (I), $A^1$ is Formula (A¹a1), wherein each $R^8$ and $R^9$ is independently selected from hydrogen, $C_{1-4}$ alkyl and $C_{6-8}$aryl; in certain embodiments, each $R^8$ and $R^9$ is independently selected from hydrogen, $C_{1-2}$alkyl, and $C_6$ aryl; and in certain embodiments, each $R^8$ and $R^9$ is hydrogen.

In certain embodiments of a compound of Formula (I), $A^1$ is Formula (A¹a2). In certain embodiments of a compound of Formula (I), $A^1$ is Formula (A¹a2), wherein $R^8$ is selected from hydrogen and $C_{1-4}$ alkyl; and in certain embodiments, $R^8$ is selected from hydrogen and methyl.

In certain embodiments of a compound of Formula (I), $A^1$ is Formula (A¹a3). In certain embodiments of a compound of Formula (I), $A^1$ is Formula (A¹a3), wherein E is selected from F, Cl, Br, and I; and in certain embodiments E is selected from Br and I.

In certain embodiments of a compound of Formula (I), $A^1$ is Formula (A¹b1). In certain embodiments of a compound of Formula (I) wherein $A^1$ is Formula (A¹b1), $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is Formula (A¹b2). In certain embodiments of a compound of Formula (I) wherein $A^1$ is Formula (A¹b2), each $R^8$ and $R^9$ is independently selected from hydrogen, $C_{1-4}$ alkyl, and $C_{6-8}$aryl; and $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl. In certain embodiments of a compound of Formula (I) wherein $A^1$ is Formula (A¹b2), each $R^8$ and $R^9$ is independently selected from hydrogen, methyl, ethyl, propyl, isopropyl, and phenyl; and $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl. In certain embodiments of a compound of Formula (I) wherein $A^1$ is Formula (A¹b2), each $R^8$ and $R^9$ is hydrogen; and $L^2$ is selected from Cl, N-hydroxysuccinimidyl, sulfo-N hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is Formula (A¹c1). In certain embodiments of a compound of Formula (I), $A^1$ is Formula (A¹c2). In certain embodiments of a compound of Formula (I), $A^1$ is Formula (A¹c3). In certain embodiments of a compound of Formula (I), $A^1$ is Formula (A¹d1). In certain embodiments of a compound of Formula (I), $A^1$ is Formula (A¹d2). In certain embodiments of a compound of Formula (I), $A^1$ is Formula (A¹d3). In certain embodiments of a compound of Formula (I), $A^1$ is Formula (A¹e1). In certain embodiments of a compound of Formula (I), $A^1$ is Formula (A¹f1). In certain embodiments of a compound of Formula (I), $A^1$ is Formula (A¹f2).

In certain embodiments of a compound of Formula (I), $X^1$ and $X^3$ are independently selected from a covalent bond, $C_{1-20}$ alkanediyl, substituted $C_{1-20}$ alkanediyl, $C_{3-12}$ cycloalkanediyl, substituted $C_{3-12}$ cycloalkanediyl, substituted $C_{3-12}$ heterocycloalkanediyl, $C_{6-20}$ arenediyl, substituted $C_{6-20}$ arenediyl, $C_{7-20}$ alkanearenediyl, substituted $C_{7-20}$ alkanearenediyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 25.

In certain embodiments of a compound of Formula (I), $X^1$ and $X^3$ are independently selected from a covalent bond, $C_{1-16}$ alkanediyl, substituted $C_{1-16}$ alkanediyl, $C_{3-6}$ cycloalkanediyl, benzene-diyl, substituted benzene-diyl, $C_{7-9}$-benzenealkane-diyl, and —$(CH_2)_{n1}$—$(CH_2$—$CH_2$—$O)_{n2}$—$(CH_2)_{n3}$—, wherein each n1 and n3 is independently an integer selected from 0 to 5 and each n2 is independently an integer selected from 1 to 20.

In certain embodiments of a compound of Formula (I), $X^1$ and $X^3$ are independently selected from a covalent bond, $C_{1-8}$ alkanediyl, substituted $C_{1-8}$ alkanediyl, $C_{3-8}$ cycloalkanediyl, benzene-diyl, substituted benzene-diyl, $C_{7-9}$-benzenealkane-diyl, and —$(CH_2)_{n1}$—$(CH_2$—$CH_2$—$O)_{n2}$—$(CH_2)_{n3}$—, wherein each n1 and n3 is independently an integer selected from 0 to 3 and each n2 is independently an integer selected from 1 to 10.

In certain embodiments of a compound of Formula (I), $X^1$ is selected from $C_{1-20}$ alkanediyl, $C_{1-20}$ cycloalkanediyl, $C_{6-10}$ arenediyl, and $C_{7-20}$ alkanearenediyl. In certain embodiments of a compound of Formula (I), $X^3$ is selected from $C_{1-20}$ alkanediyl, $C_{1-20}$ cycloalkanediyl, $C_{6-10}$ arenediyl, and $C_{7-20}$ alkanearenediyl.

In certain embodiments of a compound of Formula (I), $X^1$ is a covalent bond.

In certain embodiments of a compound of Formula (I), $X^3$ is a covalent bond.

In certain embodiments of a compound of Formula (I), $X^1$ and $X^3$ are independently selected from a covalent bond, methane-diyl, ethane-1,2-diyl, propane-1,3-diyl, butane-1,4- diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3 and each n2 is independently an integer selected from 1 to 20.

In certain embodiments of a compound of Formula (I), $X^1$ and $X^3$ are independently selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (I), $X^1$ is a covalent bond; and $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (I), $X^1$ is ethane-1,2-diyl; and $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (I), $X^1$ is pentane-1,5-diyl; and $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (I), $X^1$ is 4-methylcyclohexane-diyl; and $X^3$ is selected from a covalent bond, methane-diyl, ethane-1,2-diyl, propane-1,3-diyl, pentane-1,5-diyl, 4-methylcyclohexane-diyl, benzene-1,2-diyl, benzene-1,3-diyl, and benzene-1,4-diyl.

In certain embodiments of a compound of Formula (I) wherein $X^1$ and/or $X^3$ is —$(CH_2)_{n1}$—$(CH_2$—$CH_2$—$O)_{n2}$—$(CH_2)_{n3}$—, each n1 and n3 is independently an integer selected from 0 to 5, an integer selected from 0 to 4, an integer selected from 0 to 3, and in certain embodiments, an integer selected from 0 to 2. In certain embodiments of a compound of Formula (I) wherein $X^1$ and/or $X^3$ is —$(CH_2)_{n1}$—$(CH_2$—$CH_2$—$O)_{n2}$—$(CH_2)_{n3}$—, each n2 is independently an integer selected from 1 to 25, an integer selected from 1 to 20, an integer selected from 1 to 15, an integer selected from 1 to 10, an integer selected from 1 to 5, an integer selected from 1 to 4, and in certain embodiments, an integer selected from 1 to 3.

In certain embodiments of a compound of Formula (I), each n1 and n3 is independently an integer selected from 0 to 5, in certain embodiments, an integer selected from 0 to 4, and in certain embodiments, an integer selected from 0 to 3; and each n2 is independently an integer selected from 1 to 25, in certain embodiments an integer selected from 1 to 20, in certain embodiments an integer selected from 1 to 15, in certain embodiments an integer selected from 1 to 10, and in certain embodiments an integer selected from 1 to 5.

In certain embodiments of a compound of Formula (I), $X^2$ is selected from a covalent bond, —O—, —S—, —N—, —N=, —N=N—, —N=C—, —SO—, —$SO_2$—, —$SO_2$N—, —SS—, —C(O)—, —C(O)O—, —C(O)N—, —C(O)S—, —C(O)N—N=, —OP(O)(OH)O—, —OC(O) O—, —OC(O)N—, —NC(O)N—, and —NC(S)N. In certain embodiments of a compound of Formula (I), $X^2$ is selected from a covalent bond, —O—, —S—, —SO—, —$SO_2$—, —$SO_2$N—, —SS—, —C(O)—, —C(O)O—, —C(O)N—, —C(O)N—N=, —OC(O)N—, and —NC(O) N—. In certain embodiments of a compound of Formula (I), $X^2$ is selected from a covalent bond, —$SO_2$—, —$SO_2$N—, and —C(O)N—.

In certain embodiments of a compound of Formula (I), $R^1$ and $R^2$ are independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl.

In certain embodiments of a compound of Formula (I), $R^1$ and $R^2$ are independently selected from hydrogen, $C_{1-6}$ alkyl, substituted $C_{1-6}$ alkyl, and $C_{6-10}$ aryl. In certain embodiments of a compound of Formula (I), $R^1$ and $R^2$ are independently selected from hydrogen, methyl, ethyl, propyl, isopropyl, and phenyl. In certain embodiments of a compound of Formula (I), $R^1$ and $R^2$ are independently selected from hydrogen and methyl. In certain embodiments of a compound of Formula (I), $R^1$ and $R^2$ are independently selected from hydrogen and ethyl. In certain embodiments of a compound of Formula (I), $R^1$ and $R^2$ are independently selected from hydrogen and propyl. In certain embodiments of a compound of Formula (I), $R^1$ and $R^2$ are independently selected from hydrogen and isopropyl. In certain embodiments of a compound of Formula (I), $R^1$ and $R^2$ are independently selected from hydrogen and phenyl.

In certain embodiments of a compound of Formula (I), $R^1$ and $R^2$ are hydrogen. In certain embodiments of a compound of Formula (I), $R^1$ is hydrogen and $R^2$ is methyl. In certain embodiments of a compound of Formula (I), $R^1$ is hydrogen and $R^2$ is ethyl. In certain embodiments of a compound of Formula (I), $R^1$ is hydrogen and $R^2$ is propyl. In certain embodiments of a compound of Formula (I), $R^1$ is hydrogen and $R^2$ is isopropyl. In certain embodiments of a compound of Formula (I), $R^1$ is hydrogen and $R^2$ is phenyl.

In certain embodiments of a compound of Formula (I), $L^1$ is selected from F, Cl, Br, N-hydroxysuccinimidyl, sulfo-N-hydroxysuccinimidyl, 4-nitrophenol-yl, pentafluorophenol-yl, 4-methylsulfonylphenol-yl, hydroxybenzotriazolyl, 1-hydroxy-7-azabenzotriazolyl, trichlorophenol-yl, and imidazolyl. In certain embodiments of a compound of Formula (I), $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl. In certain embodiments of a compound of Formula (I), $L^1$ is Cl, N-hydroxysuccinimidyl, in certain embodiments, $L^1$ is sulfo-N-hydroxysuccinimidyl, in certain embodiments, $L^1$ is 4-nitrophenol-yl, in certain embodiments, $L^1$ is pentafluorophenol-yl, in certain embodiments, $L^1$ is 4-methylsulfonylphenol-yl, and in certain embodiments, $L^1$ is trichlorophenol-yl.

In certain embodiments of a compound of Formula (I), $A^1$ is a moiety of Formula ($A^1a1$), wherein each $R^8$ and $R^9$ is independently selected from hydrogen, $C_{1-4}$ alkyl, and $C_{6-10}$ aryl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2$N—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$ aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$a1), wherein each $R^8$ and $R^9$ is independently selected from hydrogen and methyl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$a1), wherein each $R^8$ and $R^9$ is hydrogen; $X^1$ is pentane-1,5-diyl; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is benzene-1,3-diyl; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is 4-methylcyclohexane-diyl; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is pentane-1,5-diyl; $X^2$ is a covalent bond; $X^3$ is a covalent bond; $R^1$ is hydrogen; $R^2$ is methyl; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is pentane-1,5-diyl; $X^2$ is a covalent bond; $X^3$ is a covalent bond; $R^1$ and $R^2$ are hydrogen; and $L^1$ is 4-nitrophenol-yl.

In certain embodiments of a compound of Formula (I), $A^1$ is a moiety of Formula ($A^1$a1), wherein each $R^8$ and $R^9$ is hydrogen; $X^1$ is benzene-1,4-diyl; $X^2$ is a covalent bond; $X^3$ is propane-1,3-diyl; $R^1$ and $R^2$ are hydrogen; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is —$(CH_2)_{n1}$—$(CH_2$—$CH_2$—$O)_{n2}$—$(CH_2)_{n3}$—, wherein n1 is 0, n2 is 2, and n3 is 2; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is pentane-1,5-diyl; $X^2$ is —C(O)N—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$a1), wherein each $R^8$ and $R^9$ is hydrogen; $X^1$ is 4-methylcyclohexane-diyl; $X^2$ is —C(O)N—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$a2), wherein $R^8$ is selected from hydrogen, $C_{1-4}$ alkyl, and $C_{6-10}$ aryl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N=N—, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$a2), wherein $R^8$ is selected from hydrogen and methyl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$a2), wherein $R^8$ is hydrogen; $X^1$ is a covalent bond; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$a2), wherein $R^8$ is methyl; $X^1$ is a covalent bond; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$a2), wherein $R^8$ is hydrogen; $X^1$ is a covalent bond; $X^2$ is —$SO_2$—; $X^3$ is methane-diyl; $R^1$ and $R^2$ are hydrogen; and $L^1$ is N-hydroxysuccinimidyl.

In certain embodiments of a compound of Formula (I), $A^1$ is a moiety of Formula ($A^1$a2), wherein $R^8$ is hydrogen; $X^1$ is a covalent bond; $X^2$ is —$SO_2$—; $X^3$ is ethane-1,2-diyl; $R^1$ and $R^2$ are hydrogen; and $L^1$ is N-hydroxysuccinimidyl.

In certain embodiments of a compound of Formula (I), $A^1$ is a moiety of Formula ($A^1$a2), wherein $R^8$ is hydrogen; $X^1$ is a covalent bond; $X^2$ is —$SO_2NH$—; $X^3$ is pentane-1,5-diyl; $R^1$ and $R^2$ are hydrogen; and $L^1$ is N-hydroxysuccinimidyl.

In certain embodiments of a compound of Formula (I), $A^1$ is a moiety of Formula ($A^1$a2), wherein $R^8$ is methyl; $X^1$ is a covalent bond; $X^2$ is —C(O)NH—; $X^3$ is pentane-1,5-diyl; $R^1$ and $R^2$ are hydrogen; and $L^1$ is N-hydroxysuccinimidyl.

In certain embodiments of a compound of Formula (I), $A^1$ is a moiety of Formula ($A^1$a2), wherein $R^8$ is methyl; $X^1$ is a covalent bond; $X^2$ is —C(O)O—; $X^3$ is pentane-1,5-diyl; $R^1$ and $R^2$ are hydrogen; and $L^1$ is N-hydroxysuccinimidyl.

In certain embodiments of a compound of Formula (I), $A^1$ is a moiety of Formula ($A^1$a3), wherein E is selected from F, Cl, Br, and I; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2$N—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$a3), wherein E is selected from F, Cl, Br, and I; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2$N—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$a3), wherein E is Br; $X^1$ is a covalent bond; $X^2$ is a covalent bond; $X^3$ is a covalent bond; $R^1$ is hydrogen; $R^2$ is methyl; and $L^1$ is N-hydroxysuccinimidyl.

In certain embodiments of a compound of Formula (I), $A^1$ is a moiety of Formula ($A^1$a3), wherein E is Br; $X^1$ is a covalent bond; $X^2$ is —C(O)NH—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$a3), wherein E is Br; $X^1$ is a covalent bond; $X^2$ is —C(O)NH—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$a3), wherein E is Br; $X^1$ is a covalent bond; $X^2$ is —C(O)O—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$b1), wherein $L^2$ is selected from halogen, N-hydroxysuccinimidyl, substituted N-hydroxysuccinimidyl, phenol-yl, and substituted phenol-yl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2$N—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$b1), wherein $L^2$ is selected from halogen, N-hydroxysuccinimidyl, substituted N-hydroxysuccinimidyl, phenol-yl, and substituted phenol-yl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2$N—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$b1), wherein $L^2$ is N-hydroxysuccinimidyl; $X^1$ is ethane-1,2-diyl; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$b2), wherein $L^2$ is selected from halogen, N-hydroxysuccinimidyl, substituted N-hydroxysuccinimidyl, phenol-yl, and substituted phenol-yl, and each $R^8$ and $R^9$ is independently selected from hydrogen, $C_{1-4}$ alkyl, and $C_{6-10}$ aryl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2$N—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$b2), wherein $L^2$ is selected from halogen, N-hydroxysuccinimidyl, substituted N-hydroxysuccinimidyl, phenol-yl, and substituted phenol-yl, and each $R^8$ and $R^9$ is independently selected from hydrogen, $C_{1-4}$ alkyl, and $C_{6-10}$ aryl; $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$b2), wherein $L^2$ is N-hydroxysuccinimidyl, and each $R^8$ and $R^9$ is hydrogen; $X^1$ is ethane-1,2-diyl; $X^2$ is a covalent bond; $X^3$ is a covalent bond; $R^1$ and $R^2$ are hydrogen; and $L^1$ is N-hydroxysuccinimidyl.

In certain embodiments of a compound of Formula (I), $A^1$ is a moiety of Formula ($A^1$c1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$c1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$c1); $X^1$ is butane-1,4-diyl; $X^2$ is a covalent bond; $X^3$ is a covalent bond; $R^1$ is hydrogen; $R^2$ is methyl; and $L^1$ is selected from N-hydroxysuccinimidyl and 4-nitrophenol-yl.

In certain embodiments of a compound of Formula (I), $A^1$ is a moiety of Formula ($A^1$c1); $X^1$ is butane-1,4-diyl; $X^2$ is a covalent bond; $X^3$ is a covalent bond; $R^1$ and $R^2$ are hydrogen; and $L^1$ is 4-nitrophenol-yl.

In certain embodiments of a compound of Formula (I), $A^1$ is a moiety of Formula ($A^1$c1); $X^1$ is butane-1,4-diyl; $X^2$ is —C(O)N—; $X^3$ is pentane-1,5-diyl; $R^1$ and $R^2$ are hydrogen; and $L^1$ is N-hydroxysuccinimidyl.

In certain embodiments of a compound of Formula (I), $A^1$ is a moiety of Formula ($A^1$c2); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$c2); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$c2); $X^1$ is butane-1,4-diyl; $X^2$ is a covalent bond; $X^3$ is a covalent bond; $R^1$ is hydrogen; $R^2$ is methyl; and $L^1$ is N-hydroxysuccinimidyl.

In certain embodiments of a compound of Formula (I), $A^1$ is a moiety of Formula ($A^1$c2); $X^1$ is butane-1,4-diyl; $X^2$ is —C(O)N—; $X^3$ is pentane-1,5-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$c2); $X^1$ is butane-1,4-diyl; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$c3); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonyl-phenol-yl, and trichlorophenol-yl.

In certain embodiments of a compound of Formula (I), $A^1$ is a moiety of Formula ($A^1$c3); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$c3); $X^1$ is butane-1,4-diyl; $X^2$ is a covalent bond; $X^3$ is a covalent bond; $R^1$ is hydrogen; $R^2$ is methyl; and $L^1$ is N-hydroxysuccinimidyl.

In certain embodiments of a compound of Formula (I), $A^1$ is a moiety of Formula ($A^1$c3); $X^1$ is butane-1,4-diyl; $X^2$ is —C(O)N—; $X^3$ is pentane-1,5-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$c3); $X^1$ is butane-1,4-diyl; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$d1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonyl-phenol-yl, and trichlorophenol-yl.

In certain embodiments of a compound of Formula (I), $A^1$ is a moiety of Formula ($A^1$d1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$d1); $X^1$ is propane-1,3-diyl; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d1); $X^1$ is propane-1,3-diyl; $X^2$ is —C(O)N—; $X^3$ is pentane-1,5-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d1); $X^1$ is propane-1,3-diyl; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$d2); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonyl-phenol-yl, and trichlorophenol-yl.

In certain embodiments of a compound of Formula (I), $A^1$ is a moiety of Formula ($A^1$d2); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$d2); $X^1$ is ethane, 1-2-diyl; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d2); $X^1$ is ethane-1,2-diyl; $X^2$ is —C(O)N—; $X^3$ is pentane-1,5-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d2); $X^1$ is ethane-1,2-diyl; $X^2$ is —C(O)N—; $X^3$ is 4-methylcyclohexane-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d3); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N═, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$d3); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$d3); $X^1$ is a covalent bond; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d3); $X^1$ is a covalent bond; $X^2$ is —C(O)N—; $X^3$ is pentane-1,5-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$d3); $X^1$ is a covalent bond; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$e1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N═, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$e1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$e1); $X^1$ is pentane-1,5-diyl; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$e1); $X^1$ is pentane-1,5-diyl; $X^2$ is —C(O)N—; $X^3$ is pentane-1,5-diyl; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$e1); $X^1$ is pentane-1,5-diyl; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$f1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 5, and each n2 is independently an integer selected from 1 to 25; $X^2$ is selected from a covalent bond, —O—, —S—, —SO—, —$SO_2$—, —$SO_2N$—, —SS—, —C(O)—, —C(O)O—, —C(O)N—, —C(O)N—N═, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$f1); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —$(CH_2)_{n1}$—$(CH_2$—$CH_2$—$O)_{n2}$—$(CH_2)_{n3}$—, wherein each n1 and n3 is independently an integer selected from 0 to 3, and each n2 is independently an integer selected from 1 to 20; $X^2$ is selected from a covalent bond, —O—, —$SO_2$—, —$SO_2N$—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$f1); $X^1$ is a covalent bond; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$f1); $X^1$ is methane-diyl; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$f1); $X^1$ is a covalent bond; $X^2$ is —C(O)N—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$f1); $X^1$ is a covalent bond; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$f1); $X^1$ is pentane-1,5-diyl; $X^2$ is —C(O)N—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$f2); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 5, and each n2 is independently an integer selected from 1 to 25; $X^2$ is selected from a covalent bond, —O—, —S—, —SO—, —SO$_2$—, —SO$_2$N—, —SS—, —C(O)—, —C(O)O—, —C(O)N—, —C(O)N—N=, —OC(O)N—, and —NC(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, 4-nitrophenol-yl, pentafluorophenol-yl, 4-methylsulfonylphenol-yl, and trichlorophenol-yl.

In certain embodiments of a compound of Formula (I), $A^1$ is a moiety of Formula ($A^1$f2); $X^1$ and $X^3$ are independently selected from a covalent bond, methane-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1'-diyl, dodecane-1,12-diyl, hexadecane-1,16-diyl, benzene-diyl, methylbenzene-diyl, propylbenzene-diyl, methylcyclohexane-diyl, and —(CH$_2$)$_{n1}$—(CH$_2$—CH$_2$—O)$_{n2}$—(CH$_2$)$_{n3}$—, wherein each n1 and n3 is independently an integer selected from 0 to 3, and each n2 is independently an integer selected from 1 to 20; $X^2$ is selected from a covalent bond, —O—, —SO$_2$—, —SO$_2$N—, —C(O)—, —C(O)O—, and —C(O)N—; $R^1$ and $R^2$ are independently selected from hydrogen, $C_{1-4}$ alkyl, and $C_{6-8}$aryl; and $L^1$ is selected from Cl, N-hydroxysuccinimidyl, sulfo-N-hydroxysuccinimidyl, and 4-nitrophenol-yl.

In certain embodiments of a compound of Formula (I), $A^1$ is a moiety of Formula ($A^1$f2); $X^1$ is methane-diyl; $X^2$ is a covalent bond; $X^3$ is a covalent bond; $R^1$ is hydrogen; $R^2$ is hydrogen; and $L^1$ is N-hydroxysuccinimidyl.

In certain embodiments of a compound of Formula (I), $A^1$ is a moiety of Formula ($A^1$f2); $X^1$ is methane-diyl; $X^2$ is —C(O)N—; $X^3$ is pentane-1,5-diyl; $R^1$ is hydrogen; $R^2$ is methyl; and $L^1$ is N-hydroxysuccinimidyl.

In certain embodiments of a compound of Formula (I), $A^1$ is a moiety of Formula ($A^1$f2); $X^1$ is methane-diyl; $X^2$ is —C(O)N—; $X^3$ is 4-methylcyclohexane-diyl; $R^1$ is hydrogen; $R^2$ is methyl; and $L^1$ is N-hydroxysuccinimidyl.

In certain embodiments of a compound of Formula (I), the compound is selected from (2,5-dioxopyrrolidin-1-yl)oxycarbonyloxymethyl 2-(2,5-dioxopyrrol-1-yl)acetate; 1-(2,5-dioxopyrrolidin-1-yl)oxycarbonyloxyethyl 2-(2,5-dioxopyrrol-1-yl)acetate; 1-(2,5-dioxopyrrolidin-1-yl)oxycarbonyloxypropyl 2-(2,5-dioxopyrrol-1-yl)acetate; 1-(2,5-dioxopyrrolidin-1-yl)oxycarbonyloxybutyl 2-(2,5-dioxopyrrol-1-yl)acetate; [1-(2,5-dioxopyrrolidin-1-yl)oxycarbonyloxy-2-methyl-propyl]2-(2,5-dioxopyrrol-1-yl)acetate; and [(2,5-dioxopyrrolidin-1-yl)oxycarbonyloxyphenyl-methyl]2-(2,5-dioxopyrrol-1-yl)acetate; or a salt of any of the foregoing.

In certain embodiments of a compound of Formula (I), the compound is selected from (2,5-dioxopyrrolidin-1-yl)oxycarbonyloxymethyl 3-(2,5-dioxopyrrol-1-yl)propanoate; 1-(2,5-dioxopyrrolidin-1-yl)oxycarbonyloxyethyl 3-(2,5-dioxopyrrol-1-yl)propanoate; 1-(2,5-dioxopyrrolidin-1-yl)oxycarbonyloxypropyl 3-(2,5-dioxopyrrol-1-yl)propanoate; 1-(2,5-dioxopyrrolidin-1-yl)oxycarbonyloxybutyl 3-(2,5-dioxopyrrol-1-yl)propanoate; [1-(2,5-dioxopyrrolidin-1-yl)oxycarbonyloxy-2-methyl-propyl]3-(2,5-dioxopyrrol-1-yl)propanoate; and [(2,5-dioxopyrrolidin-1-yl)oxycarbonyloxy-phenyl-methyl]3-(2,5-dioxopyrrol-1-yl)propanoate; or a salt of any of the foregoing.

In certain embodiments of a compound of Formula (I), the compound is selected from (2,5-dioxopyrrolidin-1-yl)oxycarbonyloxymethyl 4-(2,5-dioxopyrrol-1-yl)butanoate; 1-(2,5-dioxopyrrolidin-1-yl)oxycarbonyloxyethyl 4-(2,5-dioxopyrrol-1-yl)butanoate; 1-(2,5-dioxopyrrolidin-1-yl)oxycarbonyloxypropyl 4-(2,5-dioxopyrrol-1-yl)butanoate; 1-(2,5-dioxopyrrolidin-1-yl)oxycarbonyloxybutyl 4-(2,5-dioxopyrrol-1-yl)butanoate; [1-(2,5-dioxopyrrolidin-1-yl)oxycarbonyloxy-2-methyl-propyl]-4-(2,5-dioxopyrrol-1-yl)butanoate; and [(2,5-dioxopyrrolidin-1-yl)oxycarbonyloxyphenyl-methyl]-4-(2,5-dioxopyrrol-1-yl)butanoate; or a salt of any of the foregoing.

In certain embodiments of a compound of Formula (I), the compound is selected from (2,5-dioxopyrrolidin-1-yl)oxycarbonyloxymethyl 5-(2,5-dioxopyrrol-1-yl)pentanoate; 1-(2,5-dioxopyrrolidin-1-yl)oxycarbonyloxyethyl 5-(2,5-dioxopyrrol-1-yl)pentanoate; 1-(2,5-dioxopyrrolidin-1-yl)oxycarbonyloxypropyl 5-(2,5-dioxopyrrol-1-yl)pentanoate; 1-(2,5-dioxopyrrolidin-1-yl)oxycarbonyloxybutyl 5-(2,5-dioxopyrrol-1-yl)pentanoate; [1-(2,5-dioxopyrrolidin-1-yl)oxycarbonyloxy-2-methyl-propyl]5-(2,5-dioxopyrrol-1-yl)pentanoate; and [(2,5-dioxopyrrolidin-1-yl)oxycarbonyloxy-phenyl-methyl]5-(2,5-dioxopyrrol-1-yl)pentanoate; or a salt of any of the foregoing.

In certain embodiments of a compound of Formula (I), the compound is selected from (2,5-dioxopyrrolidin-1-yl)oxycarbonyloxymethyl 6-(2,5-dioxopyrrol-1-yl)hexanoate; 1-(2,5-dioxopyrrolidin-1-yl)oxycarbonyloxyethyl 6-(2,5-dioxopyrrol-1-yl)hexanoate; 1-(2,5-dioxopyrrolidin-1-yl)oxycarbonyloxypropyl 6-(2,5-dioxopyrrol-1-yl)hexanoate; 1-(2,5-dioxopyrrolidin-1-yl)oxycarbonyloxybutyl 6-(2,5-dioxopyrrol-1-yl)hexanoate; [1-(2,5-dioxopyrrolidin-1-yl)oxycarbonyloxy-2-methyl-propyl]6-(2,5-dioxopyrrol-1-yl)hexanoate; and [(2,5-dioxopyrrolidin-1-yl)oxycarbonyloxyphenyl-methyl]6-(2,5-dioxopyrrol-1-yl)hexanoate; or a salt of any of the foregoing.

In certain embodiments of a compound of Formula (I), the compound is selected from (2,5-dioxopyrrolidin-1-yl)oxycarbonyloxymethyl 6-[6-(2,5-dioxopyrrol-1-yl)hexanoylamino]hexanoate; 1-(2,5-dioxopyrrolidin-1-yl)oxycarbonyloxyethyl 6-[6-(2,5-dioxopyrrol-1-yl)hexanoylamino]hexanoate; 1-(2,5-dioxopyrrolidin-1-yl)oxycarbonyloxypropyl 6-[6-(2,5-dioxopyrrol-1-yl)hexanoylamino]hexanoate; 1-(2,5-dioxopyrrolidin-1-yl)oxycarbonyloxybutyl 6-[6-(2,5-dioxopyrrol-1-yl)hexanoylamino]hexanoate; [1-(2,5-dioxopyrrolidin-1-yl)oxycarbonyloxy-2-methyl-propyl]6-[6-(2,5-dioxopyrrol-1-yl)hexanoylamino]hexanoate; and [(2,5-dioxopyrrolidin-1- yl)oxycarbonyloxy-phenyl-methyl]6-[6-(2,5-dioxopyrrol-1-yl)hexanoylamino]hexanoate; or a salt of any of the foregoing.

In certain embodiments of a compound of Formula (I), the compound is selected from (2,5-dioxopyrrolidin-1-yl)oxycarbonyloxymethyl 6-[6-[6-(2,5-dioxopyrrol-1-yl)hexanoylamino]hexanoylamino]hexanoate; 1-(2,5-dioxopyrrolidin-1-yl)oxycarbonyloxyethyl 6-[6-[6-(2,5-dioxopyrrol-1-yl)hexanoylamino]hexanoylamino]hexanoate; 1-(2,5-dioxopyrrolidin-1-yl)oxycarbonyloxypropyl 6-[6-[6-(2,5-dioxopyrrol-1-yl)hexanoylamino]hexanoylamino]hexanoate; 1-(2,5-dioxopyrrolidin-1-yl)oxycarbonyloxybutyl 6-[6-[6-(2,5-dioxopyrrol-1-yl)hexanoylamino]hexanoylamino]hexanoate; [1-(2,5-dioxopyrrolidin-1-yl)oxycarbonyloxy-2-methyl-propyl]6-[6-[6-(2,5-dioxopyrrol-1-yl)hexanoylamino]hexanoylamino]hexanoate; and [(2,5-dioxopyrrolidin-1-yl)oxycarbonyloxy-phenyl-methyl] 6-[6-[6-(2,5-dioxopyrrol-1-yl)hexanoylamino]hexanoylamino]hexanoate; or a salt of any of the foregoing.

In certain embodiments of a compound of Formula (I), the compound is selected from (2,5-dioxopyrrolidin-1-yl)oxycarbonyloxymethyl 4-[(2,5-dioxopyrrol-1-yl)methyl]cyclohexanecarboxylate; 1-(2,5-dioxopyrrolidin-1-yl)oxycarbonyloxyethyl 4-[(2,5-dioxopyrrol-1-yl)methyl]cyclohexanecarboxylate; 1-(2,5-dioxopyrrolidin-1-yl)oxycarbonyloxypropyl 4-[(2,5-dioxopyrrol-1-yl)methyl]cyclohexanecarboxylate; 1-(2,5-dioxopyrrolidin-1-yl)oxycarbonyloxybutyl 4-[(2,5-dioxopyrrol-1-yl)methyl]cyclohexanecarboxylate; [1-(2,5-dioxopyrrolidin-1-yl)oxycarbonyloxy-2-methyl-propyl]-4-[(2,5-dioxopyrrol-1-yl)methyl]cyclohexanecarboxylate; and [(2,5-dioxopyrrolidin-1-yl)oxycarbonyloxy-phenyl-methyl]-4-[(2,5-dioxopyrrol-1-yl)methyl]cyclohexanecarboxylate; or a salt of any of the foregoing.

In certain embodiments of a compound of Formula (I), the compound is selected from (2,5-dioxopyrrolidin-1-yl)oxycarbonyloxymethyl 6-[[4-[(2,5-dioxopyrrol-1-yl)methyl]cyclohexanecarbonyl]amino]hexanoate; 1-(2,5-dioxopyrrolidin-1-yl)oxycarbonyloxyethyl 6-[[4-[(2,5-dioxopyrrol-1-yl)methyl]cyclohexanecarbonyl]amino]hexanoate; 1-(2,5-dioxopyrrolidin-1-yl)oxycarbonyloxypropyl 6-[[4-[(2,5-dioxopyrrol-1-yl)methyl]cyclohexanecarbonyl]amino]hexanoate; 1-(2,5-dioxopyrrolidin-1-yl)oxycarbonyloxybutyl 6-[[4-[(2,5-dioxopyrrol-1-yl)methyl]cyclohexanecarbonyl]amino]hexanoate; [1-(2,5-dioxopyrrolidin-1-yl)oxycarbonyloxy-2-methyl-propyl]6-[[4-[(2,5-dioxopyrrol-1-yl)methyl]cyclohexanecarbonyl]amino]hexanoate; and [(2,5-dioxopyrrolidin-1-yl)oxycarbonyloxy-phenyl-methyl] 6-[[4-[(2,5-dioxopyrrol-1-yl)methyl]cyclohexanecarbonyl]amino]hexanoate; or a salt of any of the foregoing.

In certain embodiments of a compound of Formula (I), the compound is selected from (2,5-dioxopyrrolidin-1-yl)oxycarbonyloxymethyl 3-(2,5-dioxopyrrol-1-yl)benzoate; 1-(2,5-dioxopyrrolidin-1-yl)oxycarbonyloxyethyl 3-(2,5-dioxopyrrol-1-yl)benzoate; 1-(2,5-dioxopyrrolidin-1-yl)oxycarbonyloxypropyl 3-(2,5-dioxopyrrol-1-yl)benzoate; 1-(2,5-dioxopyrrolidin-1-yl)oxycarbonyloxybutyl 3-(2,5-dioxopyrrol-1-yl)benzoate; [1-(2,5-dioxopyrrolidin-1-yl)oxycarbonyloxy-2-methyl-propyl] 3-(2,5-dioxopyrrol-1-yl)benzoate; and [(2,5-dioxopyrrolidin-1-yl)oxycarbonyloxy-phenyl-methyl] 3-(2,5-dioxopyrrol-1-yl)benzoate; or a salt of any of the foregoing.

In certain embodiments of a compound of Formula (I), the compound is selected from (2,5-dioxopyrrolidin-1-yl)oxycarbonyloxymethyl 4-(2,5-dioxopyrrol-1-yl)benzoate; 1-(2,5-dioxopyrrolidin-1-yl)oxycarbonyloxyethyl 4-(2,5-dioxopyrrol-1-yl)benzoate; 1-(2,5-dioxopyrrolidin-1-yl)oxycarbonyloxypropyl 4-(2,5-dioxopyrrol-1-yl)benzoate; 1-(2,5-dioxopyrrolidin-1-yl)oxycarbonyloxybutyl 4-(2,5-dioxopyrrol-1-yl)benzoate; [1-(2,5-dioxopyrrolidin-1-yl)oxycarbonyloxy-2-methyl-propyl] 4-(2,5-dioxopyrrol-1-yl)benzoate; and [(2,5-dioxopyrrolidin-1-yl)oxycarbonyloxy-phenyl-methyl] 4-(2,5-dioxopyrrol-1-yl)benzoate; or a salt of any of the foregoing.

In certain embodiments of a compound of Formula (I), the compound is selected from (2,5-dioxopyrrolidin-1-yl)oxycarbonyloxymethyl 4-[4-(2,5-dioxopyrrol-1-yl)phenyl]butanoate; 1-(2,5-dioxopyrrolidin-1-yl)oxycarbonyloxyethyl 4-[4-(2,5-dioxopyrrol-1-yl)phenyl]butanoate; 1-(2,5-dioxopyrrolidin-1-yl)oxycarbonyloxypropyl 4-[4-(2,5-dioxopyrrol-1-yl)phenyl]butanoate; 1-(2,5-dioxopyrrolidin-1-yl)oxycarbonyloxybutyl 4-[4-(2,5-dioxopyrrol-1-yl)phenyl]butanoate; [1-(2,5-dioxopyrrolidin-1-yl)oxycarbonyloxy-2-methyl-propyl] 4-[4-(2,5-dioxopyrrol-1-yl)phenyl]butanoate; and [(2,5-dioxopyrrolidin-1-yl)oxycarbonyloxy-phenyl-methyl] 4-[4-(2,5-dioxopyrrol-1-yl)phenyl]butanoate; or a salt of any of the foregoing.

In certain embodiments of a compound of Formula (I), the compound is selected from O4-(2,5-dioxopyrrolidin-1-yl) O1-[(2,5-dioxopyrrolidin-1-yl)oxycarbonyloxymethyl]butanedioate; O4-(2,5-dioxopyrrolidin-1-yl) O1-[1-(2,5-dioxopyrrolidin-1-yl)oxycarbonyloxyethyl]butanedioate; and O4-(2,5-dioxopyrrolidin-1-yl) O1-[1-(2,5-dioxopyrrolidin-1-yl)oxycarbonyloxy-2-methyl-propyl]butanedioate; or a salt of any of the foregoing.

In certain embodiments of a compound of Formula (I), the compound is selected from bis[(2,5-dioxopyrrolidin-1-yl)oxycarbonyloxymethyl]butanedioate; bis[(2,5-dioxopyrrolidin-1-yl)oxycarbonyloxymethyl]butanedioate; and bis[1-(2,5-dioxopyrrolidin-1-yl)oxycarbonyloxy-2-methyl-propyl]butanedioate; or a salt of any of the foregoing.

In certain embodiments of a compound of Formula (I), the compound is selected from (4-nitrophenoxy)carbonyloxymethyl 5-[(4S)-2-oxo-1,3,3a,4,6,6a-hexahydrothieno[3,4-d]imidazol-4-yl]pentanoate; 1-(4-nitrophenoxy)carbonyloxyethyl 5-[(4S)-2-oxo-1,3,3a,4,6,6a-hexahydrothieno[3,4-d]imidazol-4-yl]pentanoate; and [2-methyl-1-(4-nitrophenoxy)carbonyloxy-propyl] 5-[(4S)-2-oxo-1,3,3a,4,6,6a-hexahydrothieno[3,4-d]imidazo 1-4-yl]pentanoate; or a salt of any of the foregoing.

In certain embodiments of a compound of Formula (I), the compound is selected from (2,5-dioxopyrrolidin-1-yl)oxycarbonyloxymethyl 5-(5-methyl-2-oxo-imidazolidin-4-yl)pentanoate; 1-(2,5-dioxopyrrolidin-1-yl)oxycarbonyloxyethyl 5-(5-methyl-2-oxo-imidazolidin-4-yl)pentanoate; and [1-(2,5-dioxopyrrolidin-1-yl)oxycarbonyloxy-2-methyl-propyl]5-(5-methyl-2-oxo-imidazolidin-4-yl)pentanoate; or a salt of any of the foregoing.

In certain embodiments of a compound of Formula (I), the compound is selected from (2,5-dioxopyrrolidin-1-yl)oxycarbonyloxymethyl 5-[5-(5-methyl-2-oxo-imidazolidin-4-yl)pentanoylamino]pentanoate; 1-(2,5-dioxopyrrolidin-1-yl)oxycarbonyloxyethyl 5-[5-(5-methyl-2-oxo-imidazolidin-4-yl)pentanoylamino]pentanoate; and [1-(2,5-dioxopyrrolidin-1-yl)oxycarbonyloxy-2-methyl-propyl] 5-[5-(5-methyl-2-oxo-imidazolidin-4-yl)pentanoylamino]pentanoate; or a salt of any of the foregoing.

In certain embodiments of a compound of Formula (I), the compound is selected from (2,5-dioxopyrrolidin-1-yl)oxycarbonyloxymethyl 5-[(4S)-2,5,5-trioxo-1,3,3a,4,6,6a-hexahydrothieno[3,4-d]imidazol-4-yl]pentanoate; 1-(2,5-dioxopyrrolidin-1-yl)oxycarbonyloxyethyl 5-[(4S)-2,5,5-trioxo- 1,3,3a,4,6,6a-hexahydrothieno[3,4-d]imidazo-4-yl]pentanoate; and [1-(2,5-dioxopyrrolidin-1-yl)oxycarbonyloxy-2-methyl-propyl] 5-[(4S)-2,5,5-trioxo-1,3,3a,4,6,6a-hexahydrothieno[3,4-d]imidazol-4-yl]pentanoate; or a salt of any of the foregoing.

In certain embodiments of a compound of Formula (I), the compound is selected from (2,5-dioxopyrrolidin-1-yl)oxycarbonyloxymethyl 5-[5-[(4S)-2,5,5-trioxo-1,3,3a,4,6,6a-hexahydrothieno[3,4-d]imidazol-4-yl]pentanoylamino]pentanoate; 1-(2,5-dioxopyrrolidin-1-yl)oxycarbonyloxyethyl 5-[5-[(4S)-2,5,5-trioxo-1,3,3a,4,6,6a-hexahydrothieno[3,4-d]imidazo-4-yl]pentanoylamino]pentanoate; and [1-(2,5-dioxopyrrolidin-1-yl)oxycarbonyloxy-2-methyl-propyl] 5-[5-[(4S)-2,5,5-trioxo-1,3,3a,4,6,6a-hexahydrothieno[3,4-d]imidazol-4-yl]pentanoylamino]pentanoate; or a salt of any of the foregoing.

In certain embodiments of a compound of Formula (I), the compound is selected from (2,5-dioxopyrrolidin-1-yl)oxycarbonyloxymethyl 2-methylprop-2-enoate; 1-(2,5-dioxopyrrolidin-1-yl)oxycarbonyloxyethyl 2-methylprop-2-enoate; [1-(2,5-dioxopyrrolidin-1-yl)oxycarbonyloxy-2-methyl-propyl] 2-methylprop-2-enoate; (2,5-dioxopyrrolidin-1-yl)oxycarbonyloxymethyl 5-(2-methylprop-2-enoylamino)pentanoate; 1-(2,5-dioxopyrrolidin-1-yl)oxycarbonyloxyethyl 5-(2-methylprop-2-enoylamino)pentanoate; [1-(2,5-dioxopyrrolidin-1-yl)oxycarbonyloxy-2-methyl-propyl] 5-(2-methylprop-2-enoylamino)pentanoate; (2,5-dioxopyrrolidin-1-yl)oxycarbonyloxymethyl 4-[(2-methylprop-2-enoylamino)methyl]cyclohexanecarboxylate; 1-(2,5-dioxopyrrolidin-1-yl)oxycarbonyloxyethyl 4-[(2-methylprop-2-enoylamino)methyl]cyclohexanecarboxylate; and [1-(2,5-dioxopyrrolidin-1-yl)oxycarbonyloxy-2-methyl-propyl] 4-[(2-methylprop-2-enoylamino)methyl]cyclohexanecarboxylate; or a salt of any of the foregoing.

In certain embodiments of a compound of Formula (I), the compound is selected from (2,5-dioxopyrrolidin-1-yl)oxycarbonyloxymethyl prop-2-ynoate; 1-(2,5-dioxopyrrolidin-1-yl)oxycarbonyloxyethyl prop-2-ynoate; [1-(2,5-dioxopyrrolidin-1-yl)oxycarbonyloxy-2-methyl-propyl]prop-2-ynoate; (2,5-dioxopyrrolidin-1-yl)oxycarbonyloxymethyl 5-(prop-2-ynoylamino)pentanoate; 1-(2,5-dioxopyrrolidin-1-yl)oxycarbonyloxyethyl 5-(prop-2-ynoylamino)pentanoate; [1-(2,5-dioxopyrrolidin-1-yl)oxycarbonyloxy-2-methyl-propyl] 5-(prop-2-ynoylamino)pentanoate; (2,5-dioxopyrrolidin-1-yl)oxycarbonyloxymethyl 4-[(prop-2-ynoylamino)methyl]cyclohexanecarboxylate; 1-(2,5-dioxopyrrolidin-1-yl)oxycarbonyloxyethyl 4-[(prop-2-ynoylamino)methyl]cyclohexanecarboxylate; and [1-(2,5-dioxopyrrolidin-1-yl)oxycarbonyloxy-2-methyl-propyl] 4-[(prop-2-ynoylamino)methyl]cyclohexanecarboxylate; or a salt of any of the foregoing.

In certain embodiments of a compound of Formula (I), the compound is selected from (2,5-dioxopyrrolidin-1-yl)oxycarbonyloxymethyl 3-(3-methyldiazirin-3-yl)propanoate; 1-(2,5-dioxopyrrolidin-1-yl)oxycarbonyloxyethyl 3-(3-methyldiazirin-3-yl)propanoate; and [1-(2,5-dioxopyrrolidin-1-yl)oxycarbonyloxy-2-methyl-propyl] 3-(3-methyldiazirin-3-yl)propanoate; or a salt of any of the foregoing.

In certain embodiments of a compound of Formula (I), the compound is selected from (2,5-dioxopyrrolidin-1-yl)oxycarbonyloxymethyl 6-[3-(3-methyldiazirin-3-yl)propanoylamino]hexanoate; 1-(2,5-dioxopyrrolidin-1-yl)oxycarbonyloxyethyl 6-[3-(3-methyldiazirin-3-yl)propanoylamino]hexanoate; [1-(2,5-dioxopyrrolidin-1-yl)oxycarbonyloxy-2-methyl-propyl] 6-[3-(3-methyldiazirin-3-yl)propanoylamino]hexanoate; (2,5-dioxopyrrolidin-1-yl)oxycarbonyloxymethyl 4-[[3-(3-methyldiazirin-3-yl)propanoylamino]methyl]cyclohexanecarboxylate; 1-(2,5-dioxopyrrolidin-1-yl)oxycarbonyloxyethyl 4-[[3-(3-methyldiazirin-3-yl)propanoylamino]methyl]cyclohexanecarboxylate; and [1-(2,5-dioxopyrrolidin-1-yl)oxycarbonyloxy-2-methyl-propyl] 4-[[3-(3-methyldiazirin-3-yl)propanoylamino]methyl]cyclohexanecarboxylate; or a salt of any of the foregoing.

In certain embodiments of a compound of Formula (I), the compound is selected from (2,5-dioxopyrrolidin-1-yl)oxycarbonyloxymethyl 4-(7-oxofuro[3,2-g]chromen-9-yl)oxybutanoate; 1-(2,5-dioxopyrrolidin-1-yl)oxycarbonyloxyethyl 4-(7-oxofuro[3,2-g]chromen-9-yl)oxybutanoate; [1-(2,5-dioxopyrrolidin-1-yl)oxycarbonyloxy-2-methyl-propyl] 4-(7-oxofuro[3,2-g]chromen-9-yl)oxybutanoate; (2,5-dioxopyrrolidin-1-yl)oxycarbonyloxymethyl 6-[4-(7-oxofuro[3,2-g]chromen-9-yl)oxybutanoylamino]hexanoate; 1-(2,5-dioxopyrrolidin-1-yl)oxycarbonyloxyethyl 6-[4-(7-oxofuro[3,2-g]chromen-9-yl)oxybutanoylamino]hexanoate; and [1-(2,5-dioxopyrrolidin-1-yl)oxycarbonyloxy-2-methyl-propyl] 6-[4-(7-oxofuro[3,2-g]chromen-9-yl)oxybutanoylamino]hexanoate; or a salt of any of the foregoing.

In certain embodiments of a compound of Formula (I), the compound is selected from (2,5-dioxopyrrolidin-1-yl)oxycarbonyloxymethyl 2-vinylsulfonylacetate; 1-(2,5-dioxopyrrolidin-1-yl)oxycarbonyloxyethyl 2-vinylsulfonylacetate; [1-(2,5-dioxopyrrolidin-1-yl)oxycarbonyloxy-2-methyl-propyl] 2-vinylsulfonylacetate; (2,5-dioxopyrrolidin-1-yl)oxycarbonyloxymethyl 6-[(2-vinylsulfonylacetyl)amino]hexanoate; 1-(2,5-dioxopyrrolidin-1-yl)oxycarbonyloxyethyl 6-[(2-vinylsulfonylacetyl)amino]hexanoate; and [1-(2,5-dioxopyrrolidin-1-yl)oxycarbonyloxy-2-methyl-propyl] 6-[(2-vinylsulfonylacetyl)amino]hexanoate; or a salt of any of the foregoing.

In certain embodiments of a compound of Formula (I), the compound is selected from (2,5-dioxopyrrolidin-1-yl)oxycarbonyloxymethyl 2-bromoacetate; 1-(2,5-dioxopyrrolidin-1-yl)oxycarbonyloxyethyl 2-bromoacetate; [1-(2,5-dioxopyrrolidin-1-yl)oxycarbonyloxy-2-methyl-propyl] 2-bromoacetate; (2,5-dioxopyrrolidin-1-yl)oxycarbonyloxymethyl 6-[(2-bromoacetyl)amino]hexanoate; 1-(2,5-dioxopyrrolidin-1-yl)oxycarbonyloxyethyl 6-[(2-bromoacetyl)amino]hexanoate; and [1-(2,5-dioxopyrrolidin-1-yl)oxycarbonyloxy-2-methyl-propyl] 6-[(2-bromoacetyl)amino]hexanoate; or a salt of any of the foregoing.

In certain embodiments of a compound of Formula (I), the compound is selected from (2,5-dioxopyrrolidin-1-yl)oxycarbonyloxymethyl 6-azidohexanoate; 1-(2,5-dioxopyrrolidin-1-yl)oxycarbonyloxyethyl 6-azidohexanoate; [1-(2,5-dioxopyrrolidin-1-yl)oxycarbonyloxy-2-methyl-propyl] 6-azidohexanoate; (2,5-dioxopyrrolidin-1-yl)oxycarbonyloxymethyl 6-(6-azidohexanoylamino)hexanoate; 1-(2,5-dioxopyrrolidin-1-yl)oxycarbonyloxyethyl 6-(6-azidohexanoylamino)hexanoate; and [1-(2,5-dioxopyrrolidin-1-yl)oxycarbonyloxy-2-methyl-propyl] 6-(6-azidohexanoylamino)hexanoate; or a salt of any of the foregoing.

In certain embodiments of a compound of Formula (I), the compound is selected from (2,5-dioxopyrrolidin-1-yl)oxycarbonyloxymethyl 4-azidobenzoate; 1-(2,5-dioxopyrrolidin-1-yl)oxycarbonyloxyethyl 4-azidobenzoate; [1-(2,5-dioxopyrrolidin-1-yl)oxycarbonyloxy-2-methyl-propyl] 4-azidobenzoate; (2,5-dioxopyrrolidin-1-yl)oxycarbonyloxymethyl 6-[(4-azidobenzoyl)amino]hexanoate; 1-(2,5-dioxopyrrolidin-1-yl)oxycarbonyloxyethyl 6-[(4-azidobenzoyl)amino]hexanoate; and [1-(2,5-dioxopyrrolidin-1-yl)

oxycarbonyloxy-2-methyl-propyl] 6-[(4-azidobenzoyl) amino]hexanoate; or a salt of any of the foregoing.

In certain embodiments of a compound of Formula (I), the compound is selected from (2,5-dioxopyrrolidin-1-yl)oxycarbonyloxymethyl 4-azido-2-nitro-benzoate; 1-(2,5-dioxopyrrolidin-1-yl)oxycarbonyloxyethyl 4-azido-2-nitro-benzoate; [1-(2,5-dioxopyrrolidin-1-yl)oxycarbonyloxy-2-methyl-propyl] 4-azido-2-nitro-benzoate; (2,5-dioxopyrrolidin-1-yl)oxycarbonyloxymethyl 6-[(4-azido-2-nitro-benzoyl)amino]hexanoate; 1-(2,5-dioxopyrrolidin-1-yl)oxycarbonyloxyethyl 6-[(4-azido-2-nitro-benzoyl)amino]hexanoate; and [1-(2,5-dioxopyrrolidin-1-yl)oxycarbonyloxy-2-methyl-propyl] 6-[(4-azido-2-nitro-benzoyl)amino]hexanoate; or a salt of any of the foregoing.

In certain embodiments of a compound of Formula (I), the compound is selected from (2,5-dioxopyrrolidin-1-yl)oxycarbonyloxymethyl 4-azido-2-hydroxy-benzoate; 1-(2,5-dioxopyrrolidin-1-yl)oxycarbonyloxyethyl 4-azido-2-hydroxy-benzoate; [1-(2,5-dioxopyrrolidin-1-yl)oxycarbonyloxy-2-methyl-propyl] 4-azido-2-hydroxy-benzoate; (2,5-dioxopyrrolidin-1-yl)oxycarbonyloxymethyl 6-[(4-azido-2-hydroxy-benzoyl)amino]hexanoate; 1-(2,5-dioxopyrrolidin-1-yl)oxycarbonyloxyethyl 6-[(4-azido-2-hydroxy-benzoyl)amino]hexanoate; [1-(2,5-dioxopyrrolidin-1-yl)oxycarbonyloxy-2-methyl-propyl] 6-[(4-azido-2-hydroxy-benzoyl)amino]hexanoate; (2,5-dioxopyrrolidin-1-yl)oxycarbonyloxymethyl 2-(7-azido-4-methyl-2-oxo-chromen-3-yl)acetate; 1-(2,5-dioxopyrrolidin-1-yl)oxycarbonyloxyethyl 2-(7-azido-4-methyl-2-oxo-chromen-3-yl)acetate; [1-(2,5-dioxopyrrolidin-1-yl)oxycarbonyloxy-2-methyl-propyl] 2-(7-azido-4-methyl-2-oxo-chromen-3-yl)acetate; (2,5-dioxopyrrolidin-1-yl)oxycarbonyloxymethyl 6-[[2-(7-azido-4-methyl-2-oxo-chromen-3-yl)acetyl]amino]hexanoate; 1-(2,5-dioxopyrrolidin-1-yl)oxycarbonyloxyethyl 6-[[2-(7-azido-4-methyl-2-oxo-chromen-3-yl)acetyl]amino]hexanoate; and [1-(2,5-dioxopyrrolidin-1-yl)oxycarbonyloxy-2-methyl-propyl]6-[[2-(7-azido-4-methyl-2-oxo-chromen-3-yl)acetyl]amino]hexanoate; or a salt of any of the foregoing.

In certain embodiments of a compound of Formula (I), the compound is selected from (2,5-dioxopyrrolidin-1-yl)oxycarbonyloxymethyl 3-[2-[2-(2,5-dioxopyrrol-1-yl)ethoxy]ethoxy]propanoate; (2,5-dioxopyrrolidin-1-yl)oxycarbonyloxymethyl 3-[2-[2-[2-[2-(2,5-dioxopyrrol-1-yl)ethoxy]ethoxy]ethoxy]propanoate; (2,5-dioxopyrrolidin-1-yl)oxycarbonyloxymethyl 3-[2-[2-[2-[2-[2-(2,5-dioxopyrrol-1-yl)ethoxy]ethoxy]ethoxy]ethoxy]ethoxy]propanoate; (2,5-dioxopyrrolidin-1-yl)oxycarbonyloxymethyl 3-[2-[2-[2-[2-[2-[2-(2,5-dioxopyrrol-1-yl)ethoxy]ethoxy]ethoxy]ethoxy]ethoxy]ethoxy]propanoate; (2,5-dioxopyrrolidin-1-yl)oxycarbonyloxymethyl 3-[2-[2-[3-(2,5-dioxopyrrol-1-yl)propanoylamino]ethoxy]ethoxy]propanoate; (2,5-dioxopyrrolidin-1-yl)oxycarbonyloxymethyl 3-[2-[2-[2-[2-[3-(2,5-dioxopyrrol-1-yl)propanoylamino]ethoxy]ethoxy]ethoxy]ethoxy]propanoate; (2,5-dioxopyrrolidin-1-yl)oxycarbonyloxymethyl 3-[2-[2-[2-[2-[2-[3-(2,5-dioxopyrrol-1-yl)propanoylamino]ethoxy]ethoxy]ethoxy]ethoxy]ethoxy]propanoate; (2,5-dioxopyrrolidin-1-yl)oxycarbonyloxymethyl 3-[2-[2-[2-[2-[2-[2-[3-(2,5-dioxopyrro-1-yl)propanoylamino]ethoxy]ethoxy]ethoxy]ethoxy]ethoxy]ethoxy]propanoate; and (2,5-dioxopyrrolidin-1-yl)oxycarbonyloxymethyl 3-[2-[2-[2-[2-[2-[2-[2-[2-[2-[3-(2,5-dioxopyrrol-1-yl)propanoylamino]ethoxy]ethoxy]ethoxy]ethoxy]ethoxy]ethoxy]ethoxy]ethoxy]ethoxy]propanoate; or a salt of any of the foregoing.

Methods of Synthesizing Crosslinkers

Crosslinkers provided by the present disclosure may be synthesized by methods known to those skilled in the art. For example, methods of synthesizing related acyloxyalkyl carbamate compounds are described by Alexander, U.S. Pat. No. 4,760,057; Alexander, U.S. Pat. No. 4,916,230; Lund, U.S. Pat. No. 5,401,868; Alexander, U.S. Pat. No. 5,466,811; Alexander, U.S. Pat. No. 5,684,018; Gallop, U.S. Pat. No. 7,227,028, and Singh, PCT Publication No. WO 2005097760.

In certain embodiments, crosslinkers of Formula (I) may be synthesized according to the methods illustrated in Schemes 1 to 8.

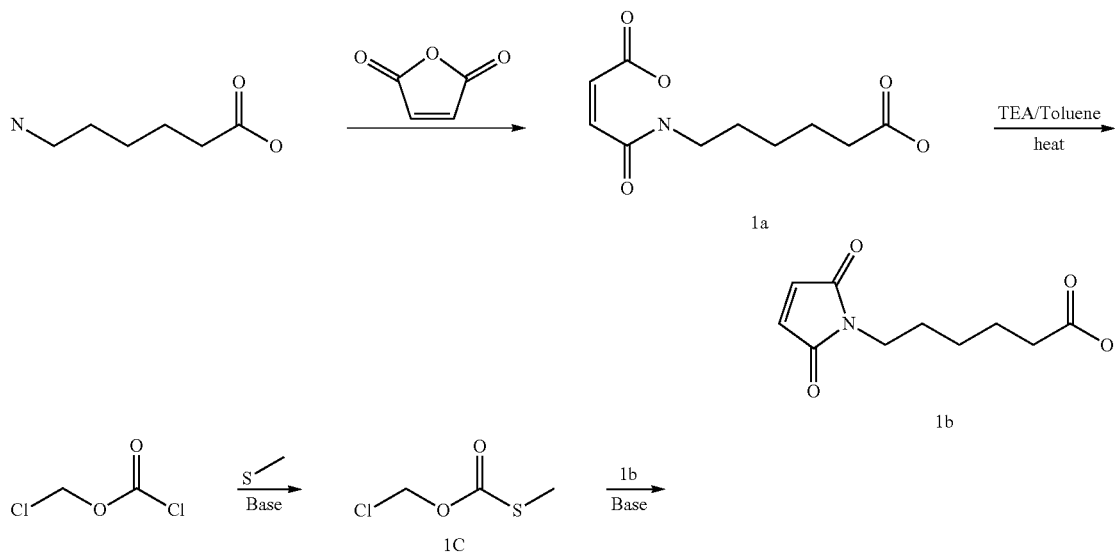

37 38
-continued
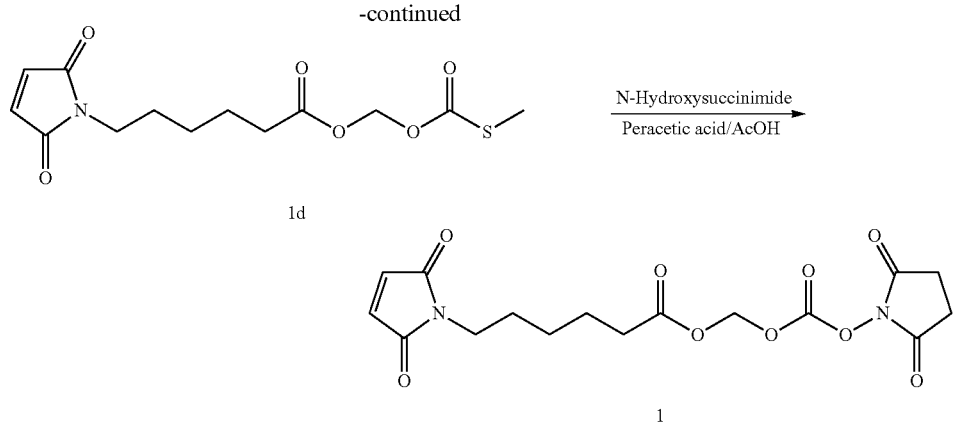
1d
1
Scheme 2
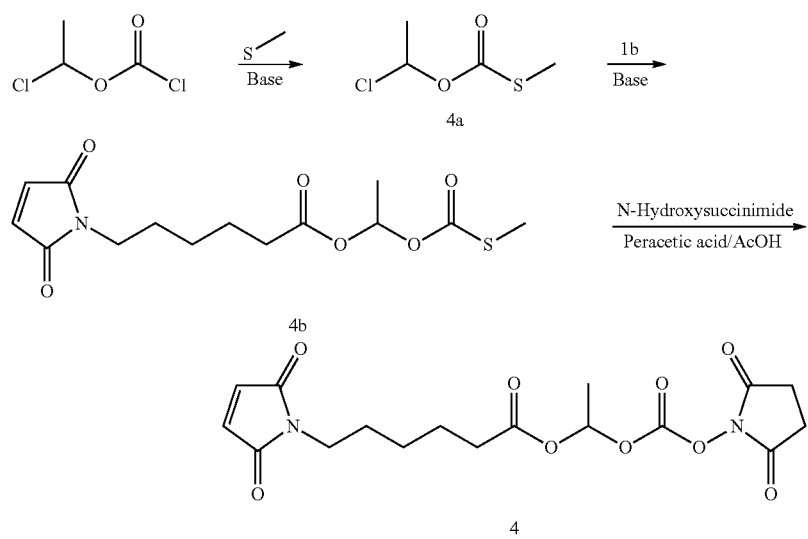
4a
4b
4
Scheme 3
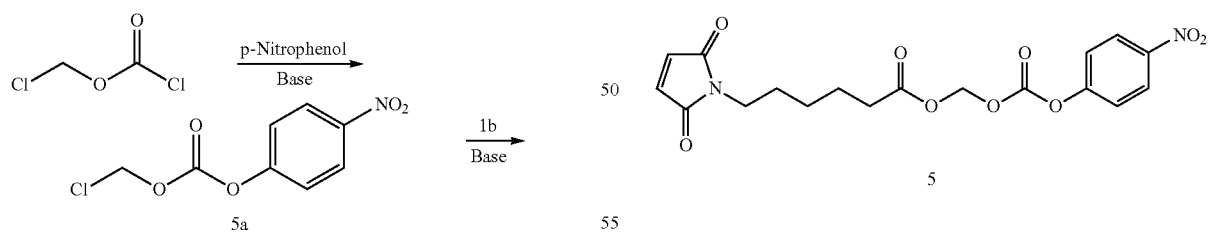
5a
5
Scheme 4
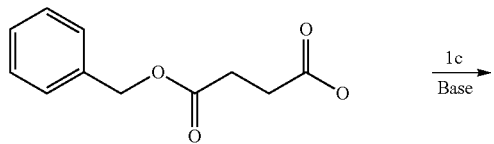

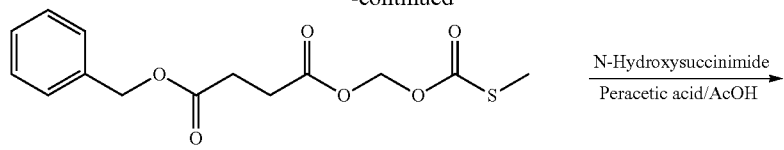
8a
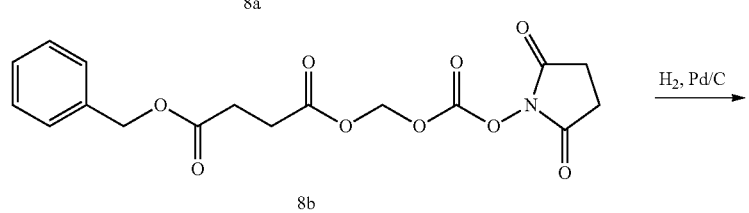
8b
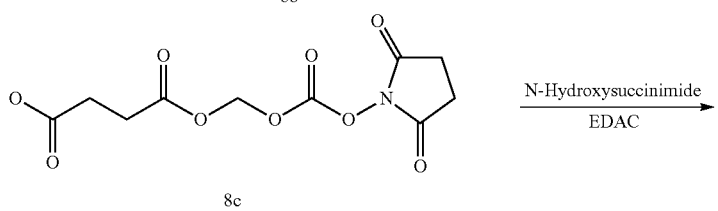
8c
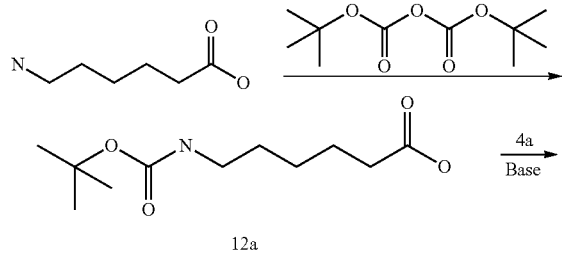
8
Scheme 5
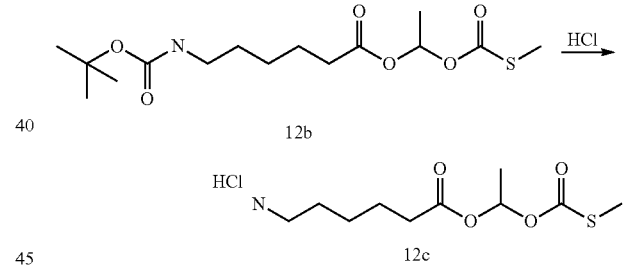
Scheme 6
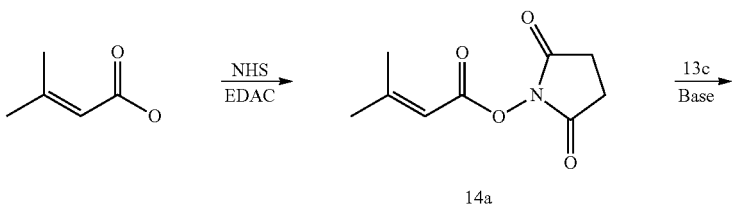
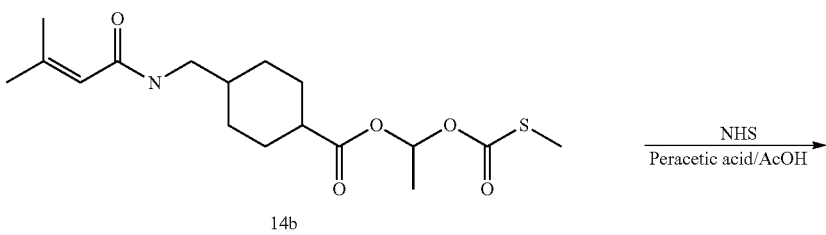

-continued
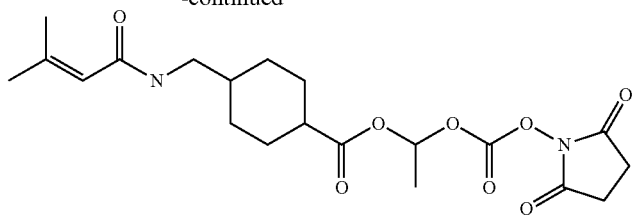
14
Scheme 7
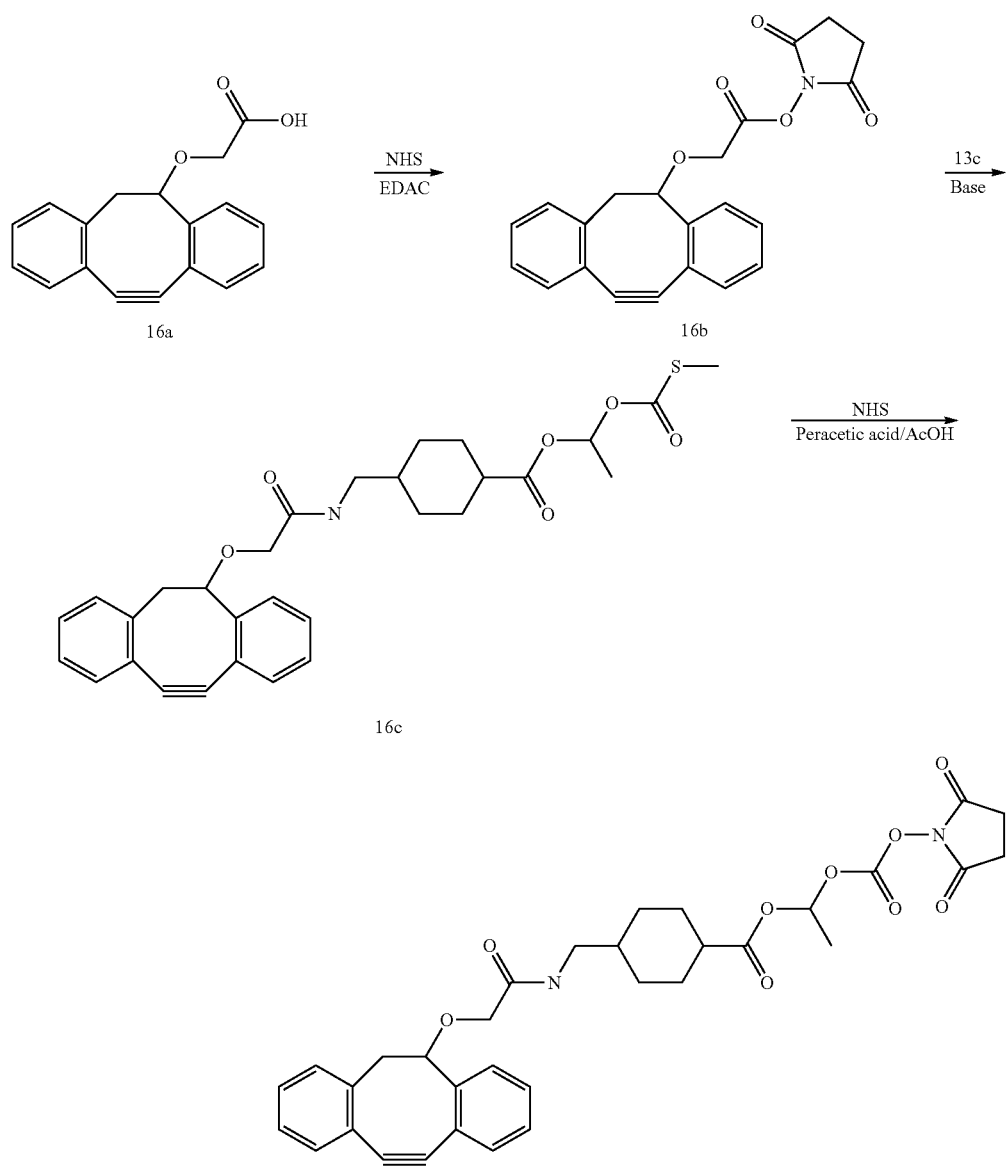

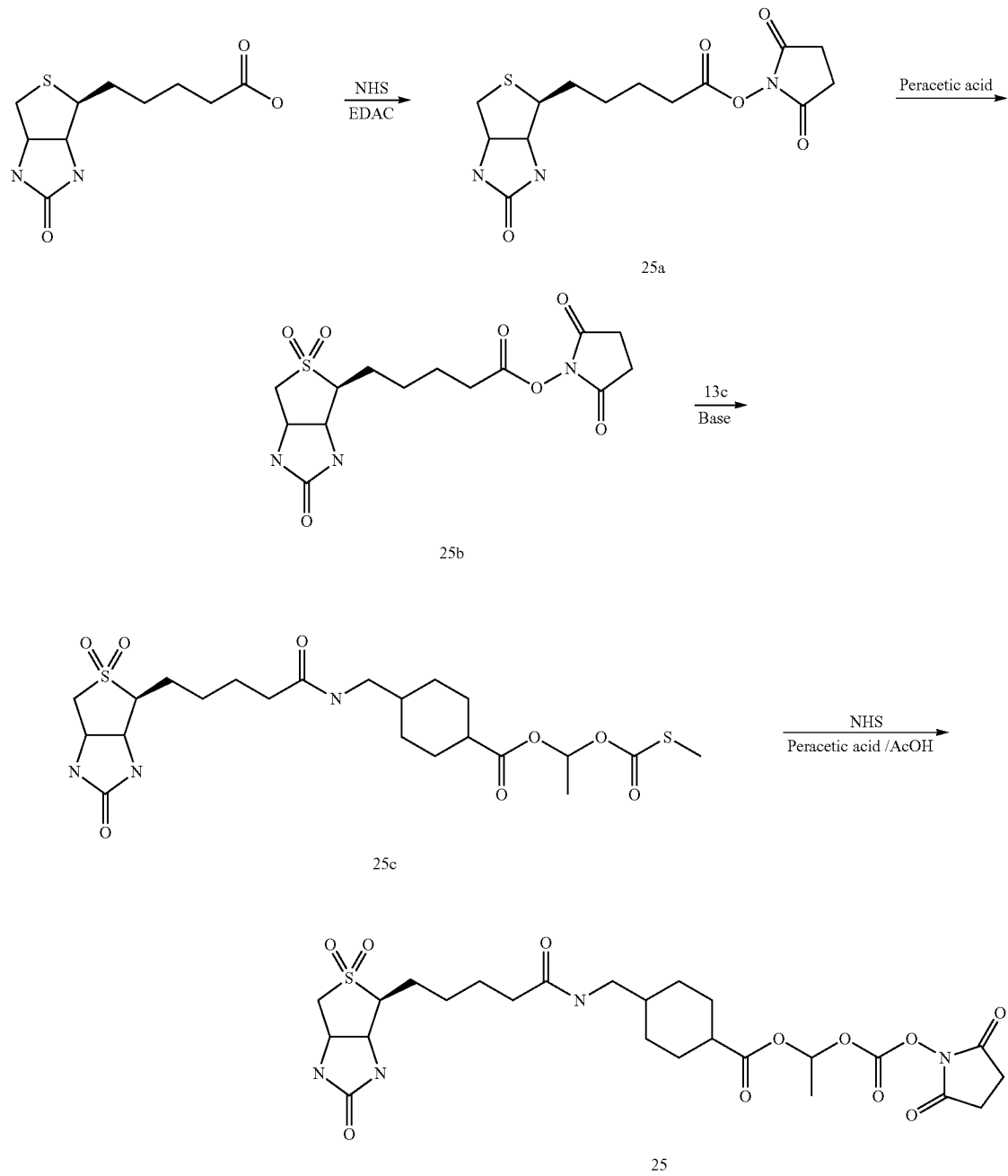
Scheme 8
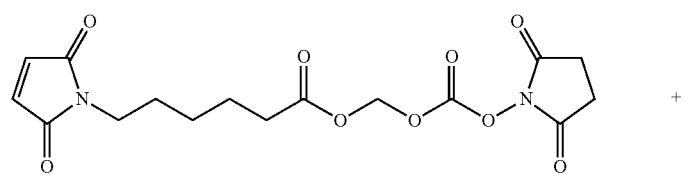
Scheme 9

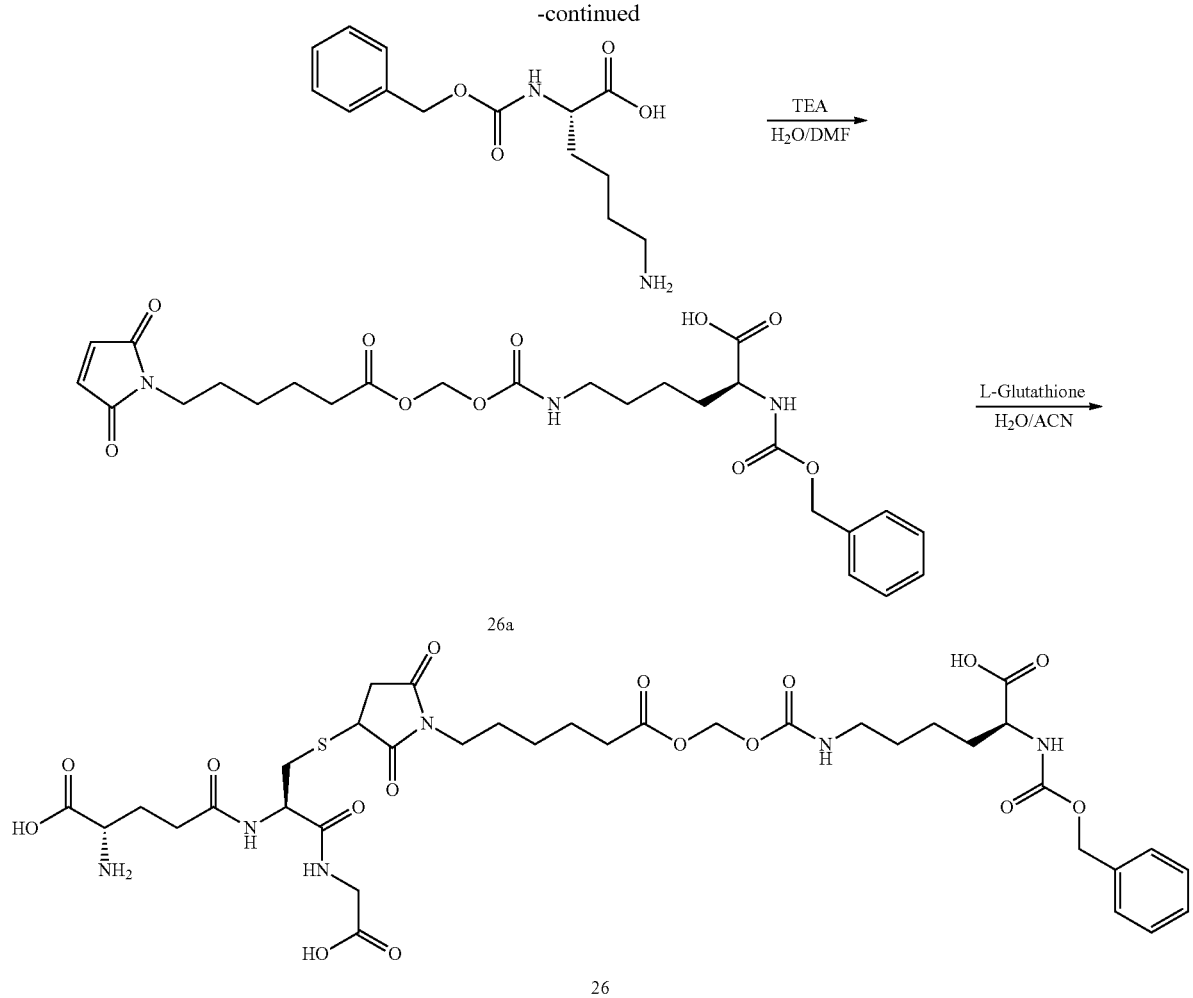

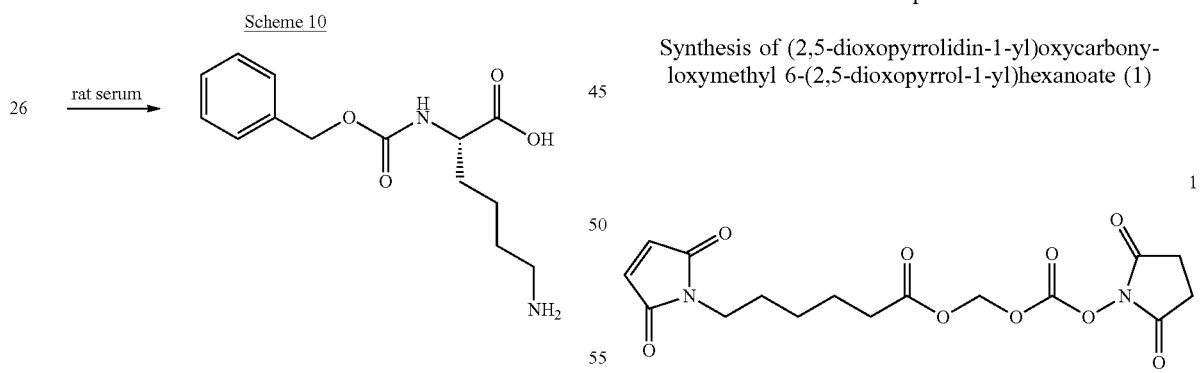

EXAMPLES

The following examples describe in detail methods of synthesizing crosslinkers and intermediates provided by the present disclosure. It will be apparent to those skilled in the art that many modifications, both to materials and methods, may be practiced without departing from the scope of the disclosure.

Example 1

Synthesis of (2,5-dioxopyrrolidin-1-yl)oxycarbonyloxymethyl 6-(2,5-dioxopyrrol-1-yl)hexanoate (1)

A solution of maleic anhydride (400 mmol, 1.0 eq) in acetic acid (200 mL) was added to a solution of aminocaproic acid (1.0 eq) in acetic acid (500 mL), and the mixture stirred at room temperature for 3 h. The white precipitate compound (1a) was filtered, washed with cold water, and dried.

A mixture of compound (1a) (15 mmol, 1.0 eq) and triethylamine (1.2 eq) in dry toluene (500 mL) was refluxed with vigorous stirring for 3 h with concomitant removal of water via a Dean-Stark apparatus. Toluene is separated from the oily residue and then concentrated under vacuum to yield a crude product (1b) as triethylammonium salt. The salt was acidified to pH 2 with aqueous HCl and product is extracted into ethyl acetate. The organic is dried over $Na_2SO_4$ and concentrated to yield compound (1b).

A mixture of 1-chloromethyl chloroformate (50 mL) and tetrabutylammonium bisulfate (25 g) in dichloromethane (350 mL) was cooled to 0° C. with an ice-water bath. A 21% solution of sodium methanethiolate (1.0 eq) in water was added. The bilayer was stirred at 0° C. for 1 h and then at room temperature for 16 h. The reaction mixture was diluted with dichloromethane, washed with water, saturated bicarbonate solution and brine, then dried over $Na_2SO_4$, filtered and concentrated in vacuo to provide compound (1c) as a colorless liquid.

A mixture of compound (1c) (0.865 g, 6.16 mmol), compound (1b) (1.00 g, 4.735 mmol), and diisopropylethylamine (DIEA) (0.825 mL, 4.735 mmol) was stirred at 70° C. for 24 h. The reaction mixture was diluted with ethyl acetate, and washed with water, saturated bicarbonate solution and brine. The organic phase was separated, dried over $Na_2SO_4$, filtered and concentrated in vacuo to yield the crude product. The crude material was then purified by silica gel column chromatography using ethyl acetate and hexanes to yield compound (1d).

To a solution of compound (1d) (0.700 g, 2.222 mmol) in dichloromethane (25 mL) was added N-hydroxysuccinimide (NHS) (0.767 g, 3.0 eq) and the reaction mixture cooled to 0° C. A solution of 32% (v/v) peracetic acid in acetic acid (1.6 g, 3.0 eq) was added dropwise over a period of 5 mins, and the solution was stirred at 0° C. for 3 h and then at room temperature overnight. The reaction mixture was then diluted with dichloromethane and washed with water, saturated sodium bicarbonate solution and brine, then dried over $Na_2SO_4$, filtered and concentrated in vacuo to give the crude product. The crude material was then purified by silica gel column chromatography using ethyl acetate and hexanes to yield compound (1). $^1$H NMR (400 MHz, $CDCl_3$): δ 1.34 (m, 2H), 1.62 (m, 2H), 1.69 (m, 2H), 2.42 (t, 2H), 2.86 (s, 4H), 3.52 (t, 2H), 5.87 (s, 2H), 6.69 (s, 2H).

Example 2

Synthesis of (2,5-dioxopyrrolidin-1-yl)oxycarbonyloxymethyl 3-(2,5-dioxopyrrol-1-yl)benzoate (2)

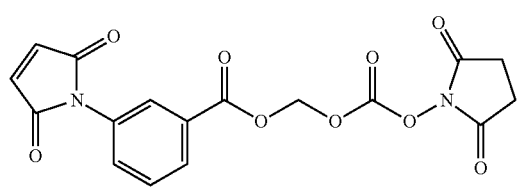

Compound (2) was prepared according to the method described in Example 1 and substituting aminocaproic acid with 3-aminobenzoic acid. $^1$H NMR (400 MHz, $CDCl_3$): δ 2.85 (s, 4H), 6.13 (s, 2H), 6.90 (s, 2H), 7.62 (m, 2H), 8.10 (m, 2H).

Example 3

Synthesis of (2,5-dioxopyrrolidin-1-yl)oxycarbonyloxymethyl 4-[(2,5-dioxopyrrol-1-yl)methyl]cyclohexanecarboxylate (3)

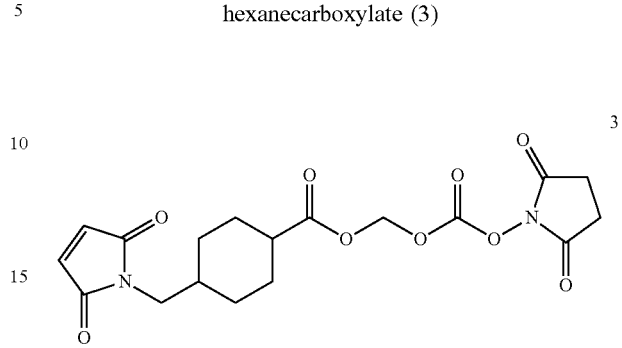

Compound (3) was prepared according to the method described in Example 1 and substituting aminocaproic acid with 4-(aminomethyl)cyclohexanecarboxylic acid. $^1$H NMR (400 MHz, $CDCl_3$): δ 1.02 (m, 2H), 1.41 (m, 2H), 1.70 (m, 1H), 1.74 (m, 2H), 2.01 (m, 2H), 2.33 (m, 1H), 2.85 (s, 4H), 3.37 (d, 2H), 5.86 (s, 2H), 6.70 (s, 2H).

Example 4

Synthesis of 1-(2,5-dioxopyrrolidin-1-yl)oxycarbonyloxyethyl 6-(2,5-dioxopyrrol-1-yl)hexanoate (4)

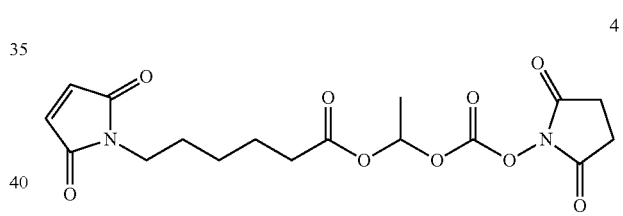

Compound (4) is prepared according to the method described in Example 1 and substituting 1-chloromethyl chloroformate with 1-chloroethyl chloroformate.

Example 5

Synthesis of (4-nitrophenoxy)carbonyloxymethyl 6-(2,5-dioxopyrrol-1-yl)hexanoate (5)

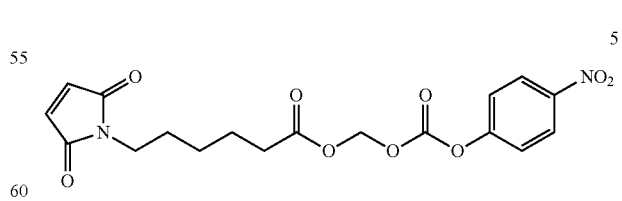

α-Chloromethylchloroformate (1.7 g, 11 mmol) is added to an ice-cold mixture of 4-nitrophenol (1.39 g, 10 mmol) and pyridine (0.8 g, 10 mmol) in dichloromethane (50 mL). The mixture is stirred at room temperature for 16 h and then diluted with dichloromethane and washed with water, 0.5% aqueous NaOH solution, water and brine. After drying over Na$_2$SO$_4$, the organic phase is concentrated under vacuum and the crude compound (5a) is crystallized from hexane.

A mixture of compound (5a), compound (1b) (1.0 eq), and AgCO$_3$ (3.0 eq) in toluene is stirred at 50° C. for 16 h. The reaction is diluted with ethyl acetate, washed with saturated bicarbonate solution and brine, dried over Na$_2$SO$_4$, and concentrated under vacuum to afford compound (5), which is then purified by silica gel using ethyl acetate and hexanes.

Example 6

Synthesis of (2,5-dioxopyrrolidin-1-yl)oxycarbonyloxymethyl 4-[4-(2,5-dioxopyrrol-1-yl)phenyl]butanoate (6)

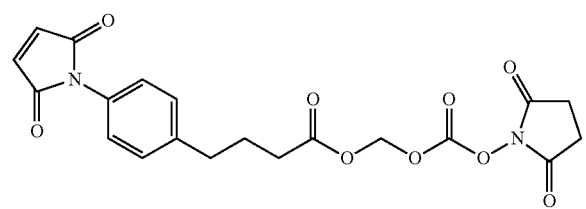

Compound (6) is prepared according to the method described in Example 1 and substituting aminocaproic acid with 4-(4-aminophenyl)butyric acid.

Example 7

Synthesis of (2,5-dioxopyrrolidin-1-yl)oxycarbonyloxymethyl 3-[2-[2-(2,5-dioxopyrrol-1-yl)ethoxy]ethoxy]propanoate (7)

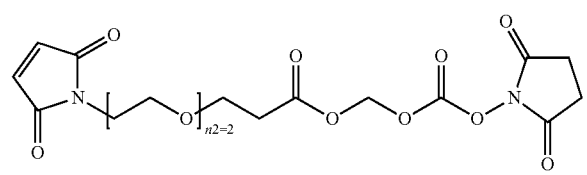

Compound (7) is prepared according to the method described in Example 1 and substituting aminocaproic acid with 3-[2-(2-aminoethoxy)ethoxy]propanoic acid.

Example 8

Synthesis of O4-(2,5-dioxopyrrolidin-1-yl) O1-[(2,5-dioxopyrrolidin-1-yl)oxycarbonyloxymethyl]butanedioate (8)

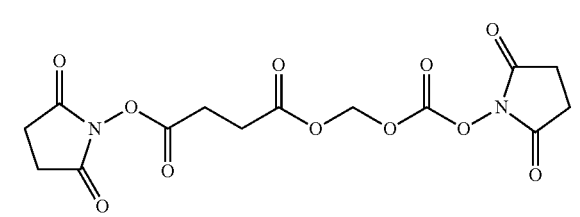

O1-Benzyl O4-[(2,5-dioxopyrrolidin-1-yl)oxycarbonyloxymethyl]butanedioate (8b) is prepared according to the method described in Example 1 and substituting compound (1b) with 4-benzyloxy-4-oxo-butanoic acid.

A mixture of compound (8b) and 10% Pd/C in ethyl acetate under a hydrogen atmosphere is stirred at room temperature for 3 h or until the reaction is completed. The mixture is filtered and the filtrate concentrated in vacuo to obtain compound (8c).

A solution of compound (8c), N-hydroxysuccinimide, and 1-ethyl-3-[3-dimethylaminopropyl]carbodiimide hydrochloride in dimethylformamide is stirred at room temperature overnight. The reaction mixture is poured into water, and the resulting precipitate is collected and dried under vacuum to afford compound (8).

Example 9

Synthesis of bis[(2,5-dioxopyrrolidin-1-yl)oxycarbonyloxymethyl]butanedioate (9)

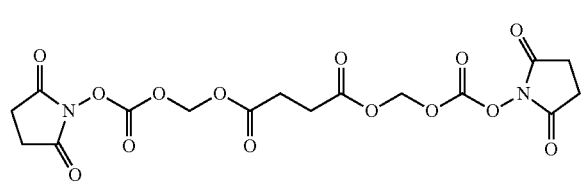

Compound (9) is prepared according to the method described in Example 1 and substituting compound (1b) with succinic acid.

Example 10

Synthesis of (4-nitrophenoxy)carbonyloxymethyl 5-[(4S)-2-oxo-1,3,3a,4,6,6a-hexahydrothieno[3,4-d]imidazol-4-yl]pentanoate (10)

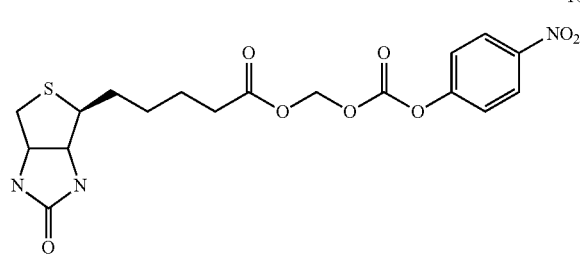

Compound (10) is prepared according to the method described in Example 5 and substituting compound (1b) with biotin.

Example 11

Synthesis of (4-nitrophenoxy)carbonyloxymethyl 5-(5-methyl-2-oxo-imidazolidin-4-yl)pentanoate (11)

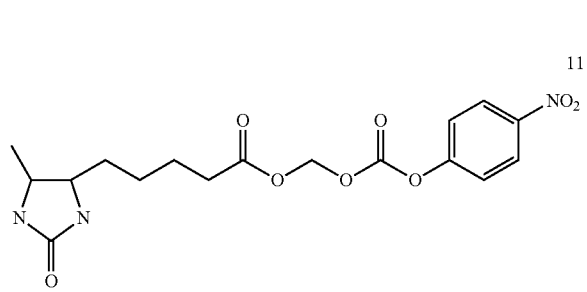 [SMILES: CC1NC(=O)NC1CCCCC(=O)OCOC(=O)Oc1ccc([N+](=O)[O-])cc1]

Compound (11) is prepared according to the method described in Example 5 and substituting compound (1b) with desthiobiotin.

Example 12

Synthesis of 1-Methylsulfanylcarbonyloxyethyl 6-aminohexanoate (12c)

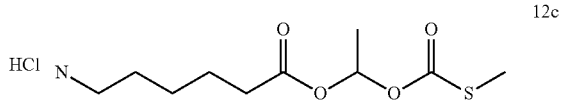 [SMILES: Cl ; CSC(=O)OC(C)OC(=O)CCCCCN]

12c

A mixture of aminocaproic acid (5.0 g) and boc anhydride (12.5 g, 1.5 eq) in methanol (100 mL) was heated at 60° C. for 2 h and then concentrated in vacuo to obtain a compound (12a).

A mixture of compound (4a) (1.25 eq), compound (12a) (1.0 eq), and triethylamine (TEA) (1.0 eq) was stirred at 70° C. overnight. The crude material was then purified by silica gel column chromatography using ethyl acetate and hexanes to yield compound (12b).

A mixture of compound (12b) (0.43 g) in 4.0 M HCl/1,4-dioxane (5.0 mL) was stirred at room temperature for 2 h and then concentrated in vacuo to obtain compound (12c) as HCl salt.

Example 13

Synthesis of 1-Methylsulfanylcarbonyloxyethyl 4-(aminomethyl)cyclohexanecarboxylate

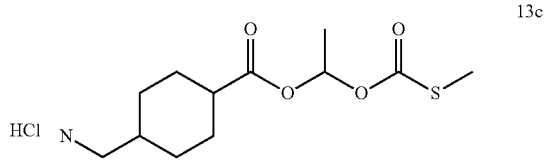 [SMILES: Cl ; CSC(=O)OC(C)OC(=O)C1CCC(CN)CC1]

13c

Compound (13c) was prepared according to the method described in Example 12 and substituting aminocaproic acid with 4-(aminomethyl)cyclohexanecarboxylic acid.

Example 14

Synthesis of 1-(2,5-dioxopyrrolidin-1-yl)oxycarbonyloxyethyl 4-[(3-methylbut-2-enoylamino)methyl]cyclohexanecarboxylate (14)

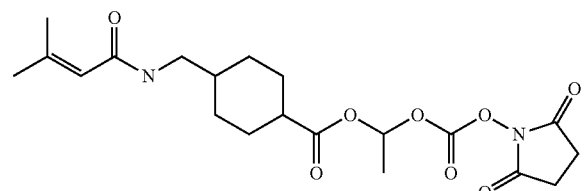

14

A mixture of 3-methylbut-2-enoic acid (2.50 g), NHS (4.27 g, 1.5 eq) and EDAC (5.7 g, 1.2 eq) in DMF (24 mL) was stirred at room temperature overnight. The mixture was concentrated in vacuo and the resulting residue was diluted with ethyl acetate (100 mL), washed with water (4×50 mL) and then dried under vacuum to obtain compound (14a).

A mixture of compound (14a) (0.2626 g), compound (13c) (0.5187 g, 1.0 eq), and TEA (0.37 mL, 2.0 eq) in DMF (5 mL) was stirred at room temperature overnight. The mixture was concentrated in vacuo and purified by silica gel using ethyl acetate and hexanes to obtain compound (14b).

A mixture of compound (14b) (100 mg), NHS (97 mg, 3.0 eq) and 32% (v/v) peracetic acid in acetic acid (176 μL, 3.0 eq) in DCM (5 mL) was stirred at room temperature overnight. The mixture was concentrated in vacuo, diluted with ethyl acetate (10 mL), washed with water (3×5 mL), and purified by silica gel using ethyl acetate and hexanes to obtain compound (14).

Example 15

Synthesis of 1-(2,5-dioxopyrrolidin-1-yl)oxycarbonyloxyethyl 4-[(prop-2-ynoylamino)methyl]cyclohexanecarboxylate (15)

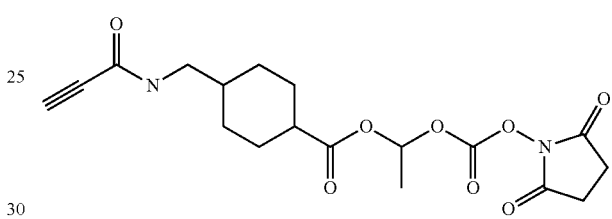

15

Compound (15) is prepared according to the method described in Example 14 and substituting 3-methylbut-2-enoic acid with prop-2-ynoic acid.

Example 16

Synthesis of dibenzocyclooctyne acyloxyalkyl NHS ester (16)

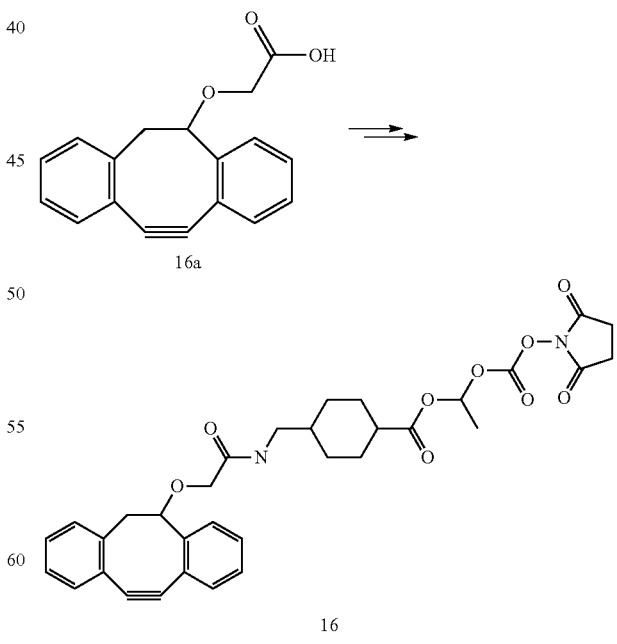

Compound (16) is prepared according to the method described in Example 14 and substituting 3-methylbut-2-enoic acid with compound (16a).

Example 17

Synthesis of 1-(2,5-dioxopyrrolidin-1-yl)oxycarbonyloxyethyl 4-[[3-(3-methyldiazirin-3-yl)propanoylamino]methyl]cyclohexanecarboxylate (17)

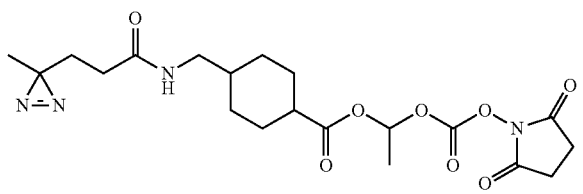

Compound (17) is prepared according to the method described in Example 14 and substituting 3-methylbut-2-enoic acid with 3-(3-methyldiazirin-3-yl)propanoic acid.

Example 18

Synthesis of 1-(2,5-dioxopyrrolidin-1-yl)oxycarbonyloxyethyl 4-[[4-(7-oxofuro[3,2-g]chromen-9-yl)oxybutanoylamino]methyl]cyclohexanecarboxylate (18)

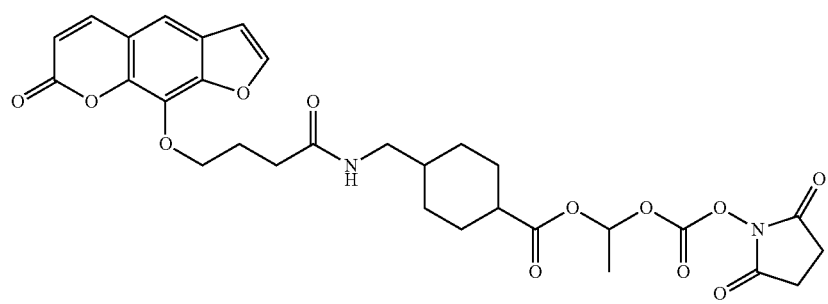

Compound (18) is prepared according to the method described in Example 14 and substituting 3-methylbut-2-enoic acid with 4-(7-oxofuro[3,2-g]chromen-9-yl)oxybutanoic acid.

Example 19

Synthesis of 1-(2,5-dioxopyrrolidin-1-yl)oxycarbonyloxyethyl 4-[[(2-vinylsulfonylacetyl)amino]methyl]cyclohexanecarboxylate (19)

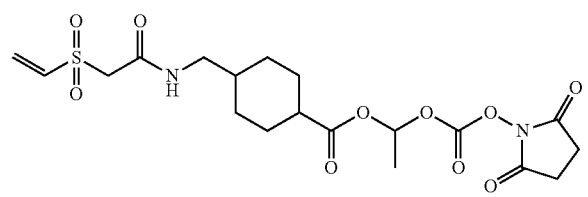

Compound (19) is prepared according to the method described in Example 14 and substituting 3-methylbut-2-enoic acid with 2-vinylsulfonylacetic acid.

Example 20

Synthesis of 1-(2,5-dioxopyrrolidin-1-yl)oxycarbonyloxyethyl 4-[[(2-bromoacetyl)amino]methyl]cyclohexanecarboxylate (20)

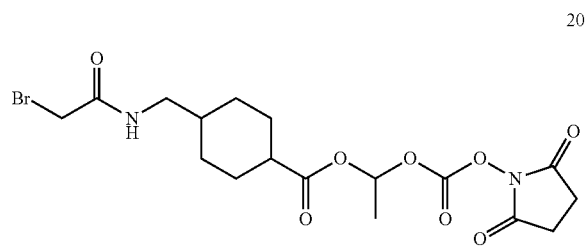 [SMILES: CC(OC(=O)ON1C(=O)CCC1=O)OC(=O)C1CCC(CNC(=O)CBr)CC1]

Compound (20) is prepared according to the method described in Example 14 and substituting 3-methylbut-2-enoic acid with bromoacetic acid.

Example 21

Synthesis of 1-(2,5-dioxopyrrolidin-1-yl)oxycarbonyloxyethyl 4-[(6-azidohexanoylamino)methyl]cyclohexanecarboxylate (21)

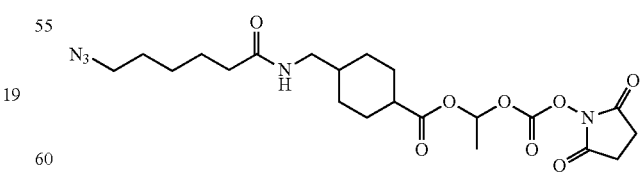

Compound (21) was prepared according to the method described in Example 14 and substituting 3-methylbut-2-enoic acid with 6-azidohexanoic acid.

Example 22

Synthesis of 1-(2,5-dioxopyrrolidin-1-yl)oxycarbonyloxyethyl 4-[[(4-azidobenzoyl)amino]methyl]cyclohexanecarboxylate (22)

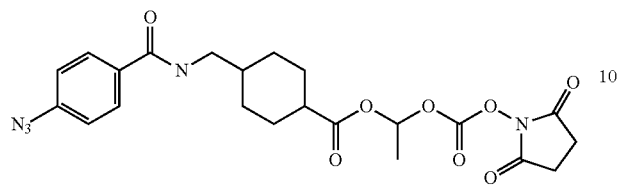

22

Compound (22) was prepared according to the method described in Example 14 and substituting 3-methylbut-2-enoic acid with 4-azidobenzoic acid.

Example 23

Synthesis of 1-(2,5-dioxopyrrolidin-1-yl)oxycarbonyloxyethyl 4-[[[2-(7-azido-4-methyl-2-oxo-chromen-3-yl)acetyl]amino]methyl]cyclohexanecarboxylate (23)

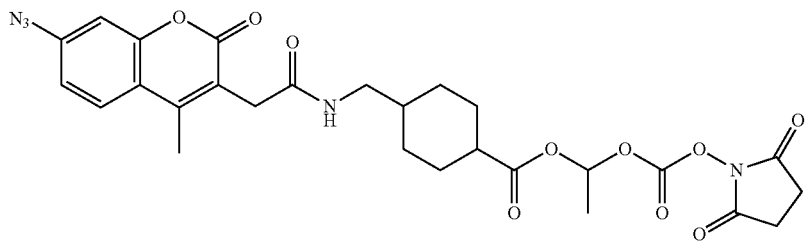

23

Compound (23) is prepared according to the method described in Example 14 and substituting 3-methylbut-2-enoic acid with 2-(7-azido-4-methyl-2-oxo-chromen-3-yl)acetic acid.

Example 24

Synthesis of 1-(2,5-dioxopyrrolidin-1-yl)oxycarbonyloxyethyl 4-[[5-(5-methyl-2-oxo-imidazolidin-4-yl)pentanoylamino]methyl]cyclohexanecarboxylate (24)

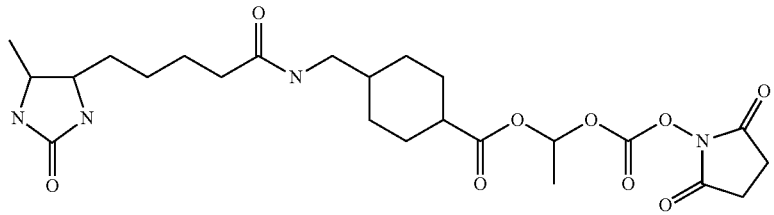

24

Compound (24) is prepared according to the method described in Example 14 and substituting 3-methylbut-2-enoic acid with desthiobiotin.

Example 25

Synthesis of 1-(2,5-dioxopyrrolidin-1-yl)oxycarbonyloxyethyl 4-[[5-[(4S)-2,5,5-trioxo-1,3,3a,4,6,6a-hexahydrothieno[3,4-d]imidazol-4-yl]pentanoylamino]methyl]cyclohexanecarboxylate (25)

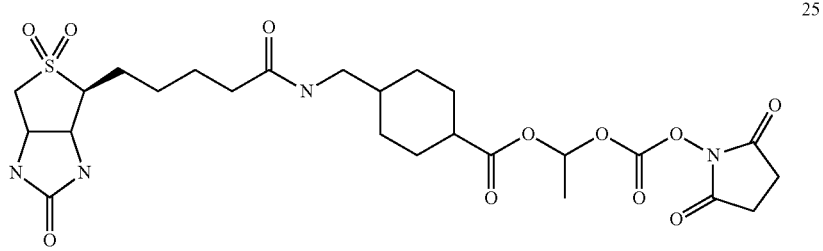 [SMILES: CC(OC(=O)ON1C(=O)CCC1=O)OC(=O)C1CCC(CNC(=O)CCCC[C@H]2C3NC(=O)NC3CS2(=O)=O)CC1]

25

A mixture of biotin (1.0 eq), NHS (1.5 eq), EDAC (1.2 eq) in DMF is stirred at room temperature overnight. The mixture is concentrated in vacuo and the resulting solid is washed with water (200 mL) and then dried under vacuum to obtain compound (25a).

A mixture of compound (25a) in 32% (v/v) peracetic acid in acetic acid is stirred at room temperature overnight. The mixture is concentrated in vacuo to obtain compound (25b).

A mixture of compound (25b) (1.0 eq) and compound (13c) (1.0 eq), TEA (2.0 eq) in DMF is stirred at room temperature overnight. The mixture is concentrated in vacuo and the resulting solid is washed with water and dried under vacuum to obtain compound (25c).

A mixture of compound (25c) and NHS (3.0 eq) in 32% (v/v) peracetic acid in acetic acid is stirred at 4° C. overnight. The mixture is concentrated in vacuo to obtain compound (25).

Example 26

Synthesis of L-glutathione $N^2$-CBZ-lysine conjugate (26)

A mixture of compound (1) (99.0 mg) and $N^2$-(carbobenzyloxy)-L-lysine (68 mg, 1.0 eq) in 1:2 water/DMF (2.5 mL) was stirred at room temperature for 30 minutes. The mixture was then concentrated in vacuo to a residue, diluted with ethyl acetate (10 mL), and washed with water (3×5 mL). The organic layer was separated and concentrated in vacuo to afford a white solid compound (26a).

A mixture of compound (26a) (8.8 mg) and L-glutathione (4.7 mg) in 1:1 water/acetonitrile (1.0 mL) was stirred at room temperature overnight to afford compound (26).

Example 27

Cleavage of Conjugate (26)

A mixture of compound (26) (2.9 mg) in potassium phosphate buffer (1.0 mL, pH 7.4) and rat serum (1.0 mL, Aleken Biologicals) was incubated at 37° C. After overnight incubation, hydrolysis of compound (26) to yield $N^2$-(carbobenzyloxy)-L-lysine was observed.

Finally, it should be noted that there are alternative ways of implementing the disclosures contained herein. Accordingly, the present embodiments are to be considered as illustrative and not restrictive, and the claims are not to be limited to the details given herein, but may be modified within the scope and equivalents thereof.

What is claimed is:

1. A compound of Formula (I):

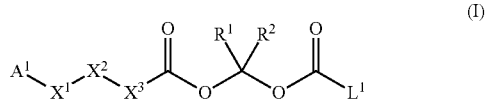

(I)

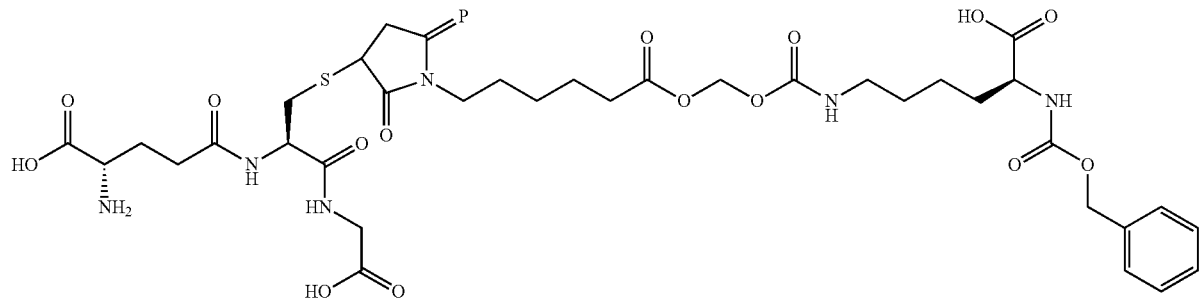

26 or a salt thereof, wherein:

$A^1$ is a moiety selected from Formula ($A^1$a1), Formula ($A^1$a2), Formula ($A^1$a3), Formula ($A^1$a4), Formula ($A^1$b1), Formula ($A^1$b3), Formula ($A^1$b4), Formula ($A^1$c1), Formula ($A^1$c2), Formula ($A^1$c3), Formula ($A^1$d1), Formula ($A^1$d2), Formula ($A^1$d3), Formula ($A^1$d4), Formula ($A^1$d5), Formula ($A^1$d6), Formula ($A^1$d7), Formula ($A^1$d8), Formula ($A^1$e1), Formula ($A^1$e2), Formula ($A^1$f1), Formula ($A^1$f2), Formula ($A^1$f3), Formula ($A^1$f4), and Formula ($A^1$f5):

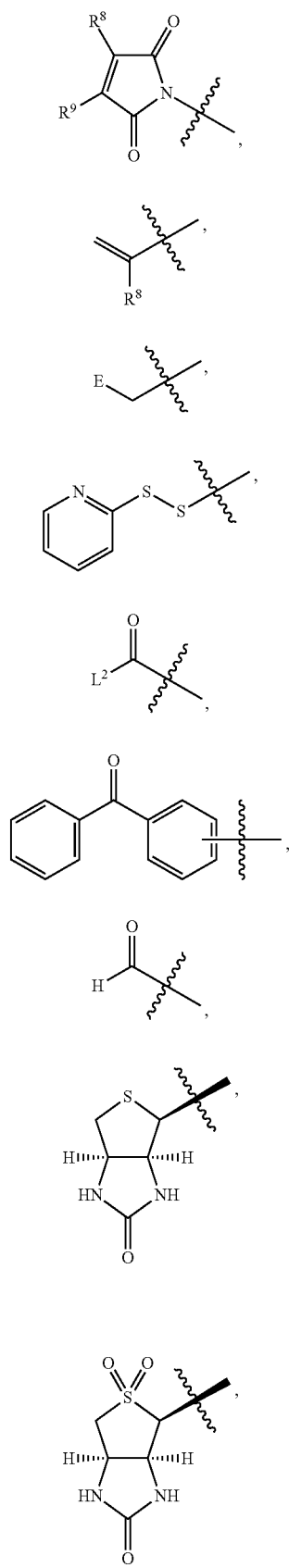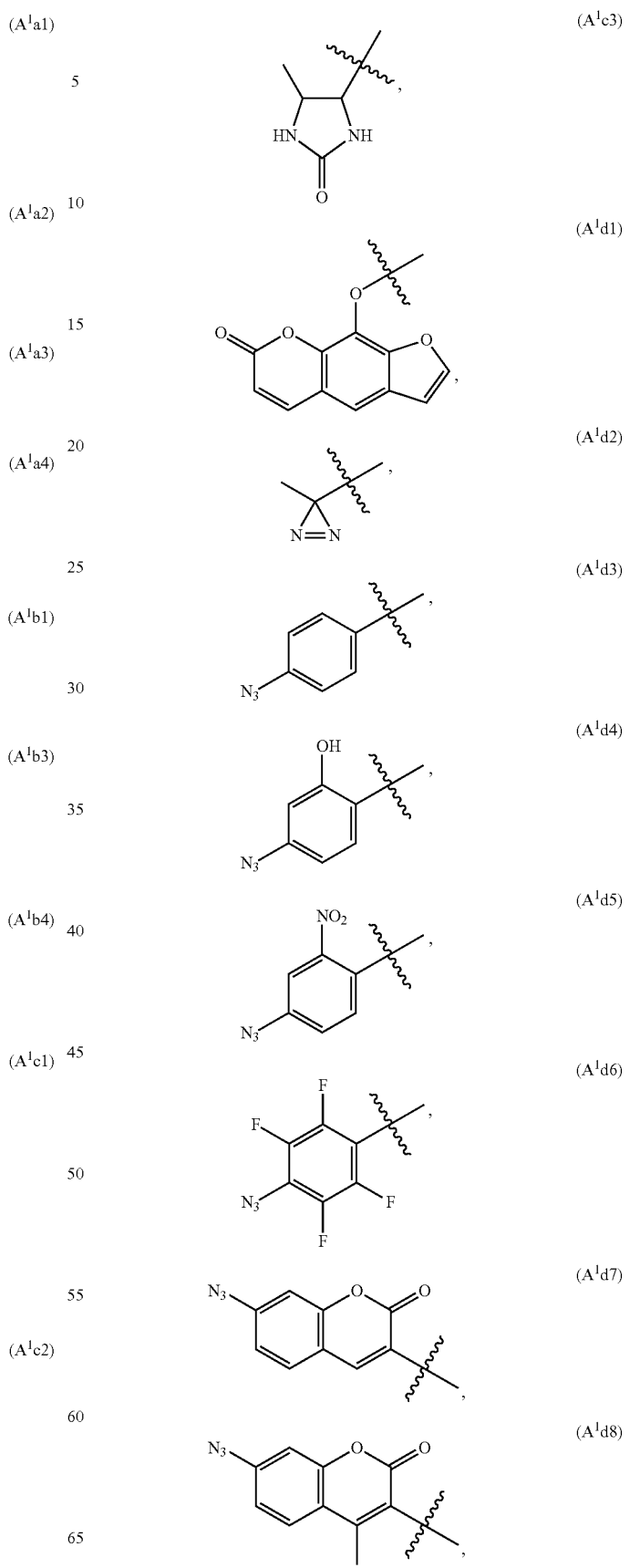

-continued

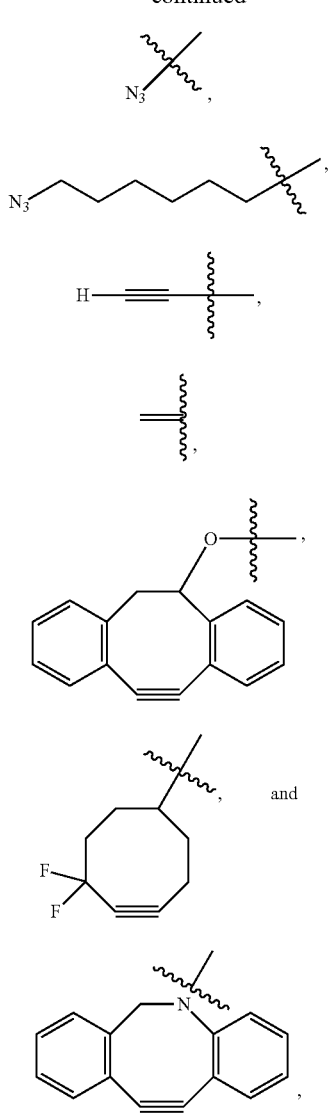

(A¹e1)

(A¹e2)

(A¹f1)

(A¹f2)

(A¹f3)

(A¹f4)

(A¹f5)

wherein:
each $R^8$ and $R^9$ is independently selected from hydrogen, methyl, ethyl, n-propyl, isopropyl, and phenyl;
each E is selected from F, Cl, Br, and I; and
each $L^2$ is selected from hydroxysuccinimidyl, phenol yl, substituted phenol yl, hydroxybenzotriazolyl, F, Cl, Br, N-hydroxysuccinimidyl, sulfo-N-hydroxysuccinimidyl, 4-nitrophenol-yl, pentafluorophenol-yl, 4-methylsulfonylphenol-yl, hydroxybenzotriazolyl, 1-hydroxy-7-azabenzotriazolyl, trichlorophenol-yl, and imidazolyl;
$X^1$ and $X^3$ are independently selected from a covalent bond, $C_{1-20}$ alkanediyl, substituted $C_{1-20}$ alkanediyl, $C_{1-20}$ heteroalkanediyl, substituted $C_{1-20}$ heteroalkanediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{4-20}$ alkanecycloalkanediyl, substituted $C_{4-20}$ alkanecycloalkanediyl, $C_{4-20}$ heteroalkanecycloalkanediyl, substituted $C_{4-20}$ heteroalkanecycloalkanediyl, $C_{6-20}$ arenediyl, substituted $C_{6-20}$ arenediyl, $C_{6-20}$ heteroarenediyl, substituted $C_{6-20}$ heteroarenediyl, $C_{7-20}$ alkanearenediyl, substituted $C_{7-20}$ alkanearenediyl, $C_{6-20}$ heteroalkanearenediyl, substituted $C_{6-20}$ heteroalkanearenediyl, and $-(CH_2)_{n1}-(CH_2-CH_2-O)_{n2}-(CH_2)-_3-$,
wherein:
each n1 and n3 is independently an integer selected from 0 to 5; and
each n2 is independently an integer selected from 1 to 25;
$X^2$ is selected from a covalent bond, —O—, —S—, —NH—, —N=, —N=N—, —N=CH—, —SO—, —SO$_2$—, —SO$_2$NH—, —SS—, —C(O)—, —C(O)O—, —C(O)NH—, —C(O)S—, —C(O)NH—N=, —OP(O)OH)O—, —OC(O)O—, —OC(O)NH—, —NHC(O)NH—, and —NHC(S)NH—;
$R^1$ and $R^2$ are independently selected from hydrogen, $C_{1-6}$ alkyl, substituted $C_{1-6}$ alkyl, $C_{1-6}$ heteroalkyl, substituted $C_{1-6}$ heteroalkyl, $C_{6-10}$ aryl, substituted $C_{6-10}$ aryl, $C_{6-10}$ heteroaryl, and substituted $C_{6-10}$ heteroaryl; and
$L^1$ is selected from F, Cl, Br, N-hydroxysuccinimidyl, sulfo-N-hydroxysuccinimidyl, 4-nitrophenol-yl, pentafluorophenol-yl, 4-methylsulfonylphenol-yl, hydroxybenzotriazolyl, 1-hydroxy-7-azabenzotriazolyl, trichlorophenol-yl, and imidazolyl;
provided that compounds falling within the following scopes of the Formula (I) are excluded:
(1) $A^1$ is $(A^{1b}3)$, $X^2$ is a covalent bond, one of $R^1$ and $R^2$ is hydrogen and the other is substituted $C_{1-6}$ alkyl, $L^1$ is 4-nitrophenol-yl, $X^1$ is substituted $C_{1-20}$ alkanediyl and $X^3$ is a covalent bond;
(2) $A^1$ is $(A^1a2)$, $R^8$ is hydrogen, $X^2$ is a covalent bond, $R^1$ and $R^2$ are hydrogen, $L^1$ is 4-nitrophenol-yl, $X^3$ is substituted $C_{1-20}$ alkanediyl and $X^1$ is a covalent bond;
(3) $A^1$ is $(A^1b1)$, L2 is Cl, $R^1$ and $R^2$ are hydrogen, $L^1$ is Cl, $X^2$ is a covalent bond, $X^3$ is $C_{1-20}$ alkanediyl, and $X^1$ is substituted $C_{1-20}$ heteroalkanediyl;
(4) $A^1$ is $(A^1a3)$, E is F, one of $R^1$ and $R^2$ is hydrogen and the other is substituted $C_{1-6}$ alkyl, $L^1$ is Cl, $X^3$ is a covalent bond, $X^2$ is —O— and $X^1$ is substituted $C_{4-20}$ heteroalkanecycloalkanediyl; and
(5) $A^1$ is $(A^1b1)$, $L^2$ is Cl, $R^1$ and $R^2$ are hydrogen, L is Cl, $X^3$ is $C_{6-20}$ arenediyl, $X^2$ is —C(O)—, and $X^1$ is $C_{1-20}$ heteroalkanediyl.

2. The compound of claim 1, wherein $A^1$ is a moiety selected from Formula (A¹a1-1), Formula (A¹a2-1), Formula (A¹a3-1), Formula (A¹a4), Formula (A¹b1-1), Formula (A¹b3), Formula (A¹b4), Formula (A¹c1), Formula (A¹c2), Formula (A¹c3), Formula (A¹d1), Formula (A¹d2), Formula (A¹d3), Formula (A¹e1), Formula (A¹e2), Formula (A¹f1), Formula (A¹f3), Formula (A¹f4), and Formula (A¹f5):

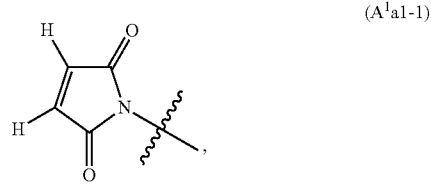

(A¹a1-1)

(A¹a2-1)

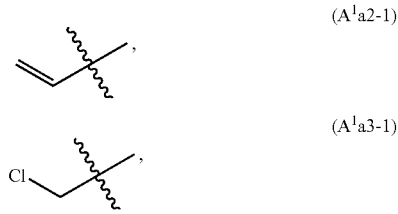

(A¹a3-1)

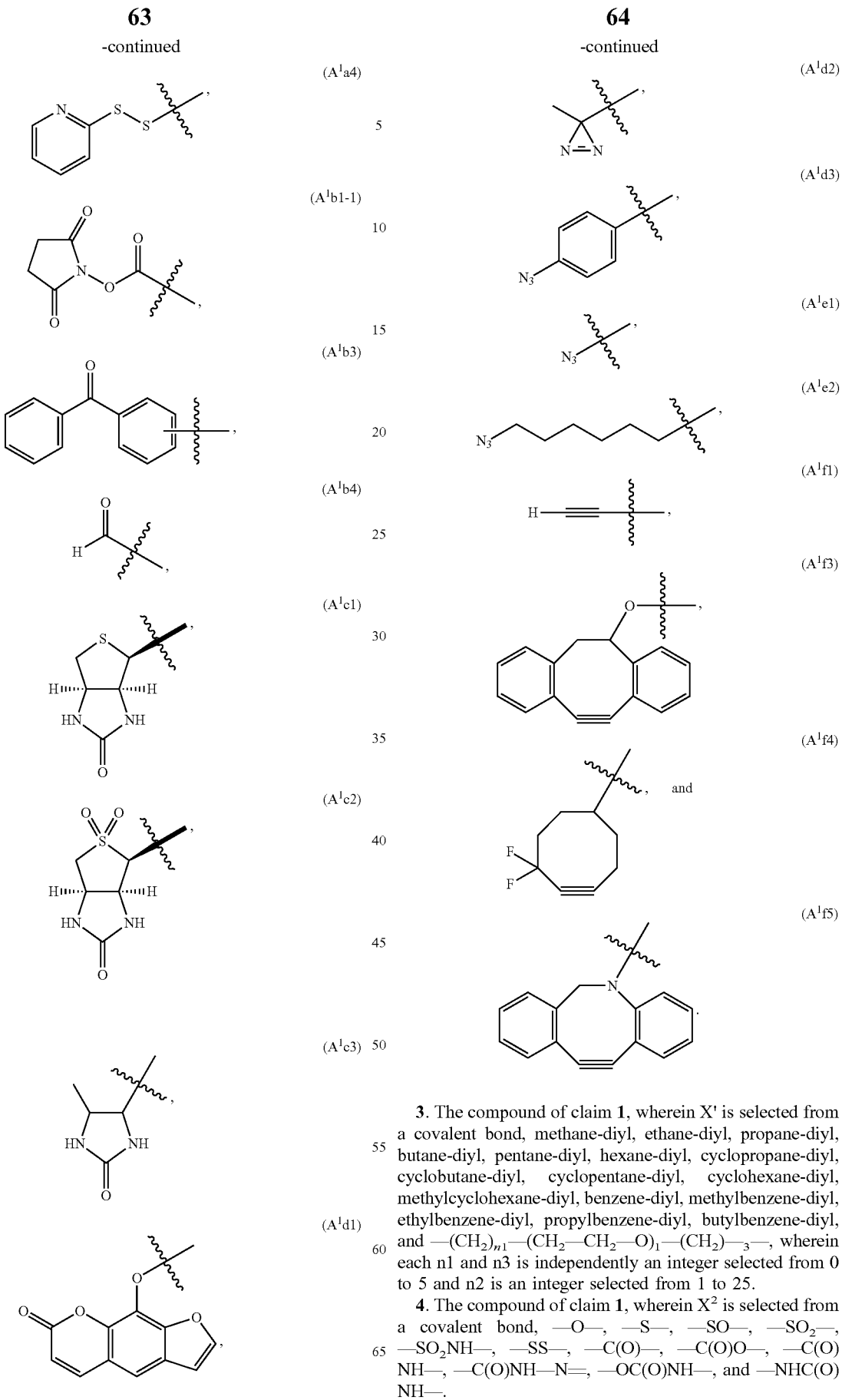

3. The compound of claim 1, wherein X¹ is selected from a covalent bond, methane-diyl, ethane-diyl, propane-diyl, butane-diyl, pentane-diyl, hexane-diyl, cyclopropane-diyl, cyclobutane-diyl, cyclopentane-diyl, cyclohexane-diyl, methylcyclohexane-diyl, benzene-diyl, methylbenzene-diyl, ethylbenzene-diyl, propylbenzene-diyl, butylbenzene-diyl, and —(CH$_2$)$_{n1}$—(CH$_2$—CH$_2$—O)$_1$—(CH$_2$)—$_3$—, wherein each n1 and n3 is independently an integer selected from 0 to 5 and n2 is an integer selected from 1 to 25.

4. The compound of claim 1, wherein X² is selected from a covalent bond, —O—, —S—, —SO—, —SO$_2$—, —SO$_2$NH—, —SS—, —C(O)—, —C(O)O—, —C(O)NH—, —C(O)NH—N=, —OC(O)NH—, and —NHC(O)NH—.

5. The compound of claim 1, wherein $X^3$ is selected from a covalent bond, methane-diyl, ethane-diyl, propane-diyl, butane-diyl, pentane-diyl, hexane-diyl, cyclopropane-diyl, cyclobutane-diyl, cyclopentane-diyl, cyclohexane-diyl, methylcyclohexane-diyl, benzene-diyl, methylbenzene-diyl, ethylbenzene-diyl, propylbenzene-diyl, butylbenzene-diyl, and —$(CH_2)_{n1}$—$(CH_2$—$CH_2$—$O)_{n2}$—$(CH_2)_{n3}$—, wherein each n1 and n3 is independently an integer selected from 0 to 5 and n2 is an integer selected from 1 to 25.

6. The compound of claim 1, wherein $R^1$ and $R^2$ are independently selected from hydrogen, methyl, ethyl, propyl, isopropyl, and phenyl.

7. The compound of claim 1, wherein $L^1$ is selected from Cl, N-hydroxysuccinimidyl, sulfo-N-hydroxysuccinimidyl, 4-nitrophenol-yl, and pentafluorophenol-yl.

8. The compound of claim 1, wherein the compound is selected from (2,5-dioxopyrrolidin-1-yl)oxycarbonyloxymethyl 2-(2,5-dioxopyrrol-1-yl)acetate; (2,5-dioxopyrrolidin-1-yl)oxycarbonyloxymethyl 3-(2,5-dioxopyrrol-1-yl)propanoate; (2,5-dioxopyrrolidin-1-yl)oxycarbonyloxymethyl 4-(2,5-dioxopyrrol-1-yl)butanoate; (2,5-dioxopyrrolidin-1-yl)oxycarbonyloxymethyl 5-(2,5-dioxopyrrol-1-yl)pentanoate; (2,5-dioxopyrrolidin-1-yl)oxycarbonyloxymethyl 6-(2,5-dioxopyrrol-1-yl)hexanoate; 1-(2,5-dioxopyrrolidin-1-yl)oxycarbonyloxyethyl 6-(2,5-dioxopyrrol-1-yl)hexanoate; [1-(2,5-dioxopyrrolidin-1-yl)oxycarbonyloxy-2-methyl-propyl] 6-(2,5-dioxopyrrol-1-yl)hexanoate; (2,5-dioxopyrrolidin-1-yl)oxycarbonyloxymethyl 6-[6-(2,5-dioxopyrrol-1-yl)hexanoylamino]hexanoate; (2,5-dioxopyrrolidin-1-yl)oxycarbonyloxymethyl 6-[6-[6-(2,5-dioxopyrrol-1-yl)hexanoylamino]hexanoylamino]hexanoate; (2,5-dioxopyrrolidin-1-yl)oxycarbonyloxymethyl 4-[(2,5-dioxopyrrol-1-yl)methyl]cyclohexanecarboxylate; 1-(2,5-dioxopyrrolidin-1-yl)oxycarbonyloxyethyl 4-[(2,5-dioxopyrrol-1-yl)methyl]cyclohexanecarboxylate; [1-(2,5-dioxopyrrolidin-1-yl)oxycarbonyloxy-2-methyl-propyl] 4-[(2,5-dioxopyrrol-1-yl)methyl]cyclohexanecarboxylate; (2,5-dioxopyrrolidin-1-yl)oxycarbonyloxymethyl 6-[[4-[(2,5-dioxopyrrol-1-yl)methyl]cyclohexanecarbonyl]amino] hexanoate; (2,5-dioxopyrrolidin-1-yl)oxycarbonyloxymethyl 3-(2,5-dioxopyrrol-1-yl)benzoate; (2,5-dioxopyrrolidin-1-yl)oxycarbonyloxymethyl 4-(2,5-dioxopyrrol-1-yl)benzoate; (2,5-dioxopyrrolidin-1-yl)oxycarbonyloxymethyl 4-[4-(2,5-dioxopyrrol-1-yl)phenyl]butanoate; O4-(2,5-dioxopyrrolidin-1-yl) O1-[(2,5-dioxopyrrolidin-1-yl)oxycarbonyloxymethyl] butanedioate; (4-nitrophenoxy)carbonyloxymethyl 5-[(4S)-2-oxo-1,3,3a,4,6,6a-hexahydrothieno[3,4-d]imidazol-4-yl]pentanoate; (2,5-dioxopyrrolidin-1-yl)oxycarbonyloxymethyl 5-(5-methyl-2-oxo-imidazolidin-4-yl)pentanoate; (2,5-dioxopyrrolidin-1-yl)oxycarbonyloxymethyl 6-[5-(5-methyl-2-oxo-imidazolidin-4-yl)pentanoylamino]hexanoate; (2,5-dioxopyrrolidin-1-yl)oxycarbonyloxymethyl 5-[(4S)-2,5,5-trioxo-1,3,3a,4,6,6a-hexahydrothieno[3,4-d]imidazol-4-yl]pentanoate; (2,5-dioxopyrrolidin-1-yl)oxycarbonyloxymethyl 6-[5-[(4S)-2,5,5-trioxo-1,3,3a,4,6,6a-hexahydrothieno[3,4-d]imidazol-4-yl]pentanoylamino]hexanoate; (2,5-dioxopyrrolidin-1-yl)oxycarbonyloxymethyl 2-methylprop-2-enoate; (2,5-dioxopyrrolidin-1-yl)oxycarbonyloxymethyl 6-(2-methylprop-2-enoylamino)hexanoate; (2,5-dioxopyrrolidin-1-yl)oxycarbonyloxymethyl prop-2-ynoate; (2,5-dioxopyrrolidin-1-yl)oxycarbonyloxymethyl 6-(prop-2-ynoylamino)hexanoate; (2,5-dioxopyrrolidin-1-yl)oxycarbonyloxymethyl 3-(3-methyldiazirin-3-yl)propanoate; (2,5-dioxopyrrolidin-1-yl)oxycarbonyloxymethyl 6-[3-(3-methyldiazirin-3-yl)propanoylamino]hexanoate; (2,5-dioxopyrrolidin-1-yl)oxycarbonyloxymethyl 4-(7-oxofuro[3,2-g]chromen-9-yl)oxybutanoate; (2,5-dioxopyrrolidin-1-yl)oxycarbonyloxymethyl 2-vinyl sulfonylacetate; (2,5-dioxopyrrolidin-1-yl)oxycarbonyloxymethyl 6-[(2-vinylsulfonylacetyl)amino]hexanoate; (2,5-dioxopyrrolidin-1-yl)oxycarbonyloxymethyl 6-[(2-bromoacetyl)amino]hexanoate; (2,5-dioxopyrrolidin-1-yl)oxycarbonyloxymethyl 6-azidohexanoate; (2,5-dioxopyrrolidin-1-yl)oxycarbonyloxymethyl 6-(6-azidohexanoylamino)hexanoate; (2,5-dioxopyrrolidin-1-yl)oxycarbonyloxymethyl 4-azidobenzoate; (2,5-dioxopyrrolidin-1-yl)oxycarbonyloxymethyl 6-[(4-azidobenzoyl)amino]hexanoate; (2,5-dioxopyrrolidin-1-yl)oxycarbonyloxymethyl 4-azido-2-nitro-benzoate; (2,5-dioxopyrrolidin-1-yl)oxycarbonyloxymethyl 6-[(4-azido-2-nitro-benzoyl)amino]hexanoate; (2,5-dioxopyrrolidin-1-yl)oxycarbonyloxymethyl 4-azido-2-hydroxy-benzoate; (2,5-dioxopyrrolidin-1-yl)oxycarbonyloxymethyl 6-[(4-azido-2-hydroxy-benzoyl)amino]hexanoate; (2,5-dioxopyrrolidin-1-yl)oxycarbonyloxymethyl 2-(7-azido-4-methyl-2-oxo-chromen-3-yl)acetate; (2,5-dioxopyrrolidin-1-yl)oxycarbonyloxymethyl 6-[[2-(7-azido-4-methyl-2-oxo-chromen-3-yl)acetyl]amino] hexanoate; (4-nitrophenoxy)carbonyloxymethyl 6-(2,5-dioxopyrrol-1-yl)hexanoate; (2,5-dioxopyrrolidin-1-yl)oxycarbonyloxymethyl 3-[2-[2-(2,5-dioxopyrrol-1-yl)ethoxy]ethoxy]propanoate; O4-(2,5-dioxopyrrolidin-1-yl) O1-[(2,5-dioxopyrrolidin-1-yl)oxycarbonyloxymethyl] butanedioate; (4-nitrophenoxy)carbonyloxymethyl 5-(5-methyl-2-oxo-imidazolidin-4-yl)pentanoate; 1-(2,5-dioxopyrrolidin-1-yl)oxycarbonyloxyethyl 4-[(prop-2-ynoylamino)methyl]cyclohexanecarboxylate; 1-(2,5-dioxopyrrolidin-1-yl)oxycarbonyloxyethyl 4-[[3-(3-methyldiazirin-3-yl)propanoylamino]methyl]cyclohexanecarboxylate; 1-(2,5-dioxopyrrolidin-1-yl)oxycarbonyloxyethyl 4-[[4-(7-oxofuro[3,2-g]chromen-9-yl)oxybutanoylamino]methyl]cyclohexanecarboxylate; 1-(2,5-dioxopyrrolidin-1-yl)oxycarbonyloxyethyl 4-[[(2-vinylsulfonylacetyl)amino]methyl]cyclohexanecarboxylate; 1-(2,5-dioxopyrrolidin-1-yl)oxycarbonyloxyethyl 4-[[(2-bromoacetyl)amino]methyl]cyclohexanecarboxylate; 1-(2,5-dioxopyrrolidin-1-yl)oxycarbonyloxyethyl 4-[(6-azidohexanoylamino)methyl]cyclohexanecarboxylate; 1-(2,5-dioxopyrrolidin-1-yl)oxycarbonyloxyethyl 4-[[(4-azidobenzoyl)amino]methyl]cyclohexanecarboxylate; 1-(2,5-dioxopyrrolidin-1-yl)oxycarbonyloxyethyl 4-[[[2-(7-azido-4-methyl-2-oxo-chromen-3-yl)acetyl]amino]methyl] cyclohexanecarboxylate; 1-(2,5-dioxopyrrolidin-1-yl)oxycarbonyloxyethyl 4-[[5-(5-methyl-2-oxo-imidazolidin-4-yl)pentanoylamino]methyl]cyclohexanecarboxylate; and 1-(2,5-dioxopyrrolidin-1-yl)oxycarbonyloxyethyl 4-[[5-[(4S)-2,5,5-trioxo-1,3,3a,4,6,6a-hexahydrothieno[3,4-d]imidazol-4-yl]pentanoylamino]methyl]cyclohexanecarboxylate; or a salt of any of the foregoing.

9. The compound 1-(2,5-dioxopyrrolidin-1-yl)oxycarbonyloxyethyl 4-[(3-methylbut-2-enoylamino)methyl]cyclohexanecarboxylate.

* * * * *